US012661405B2

(12) United States Patent
Whiting et al.

(10) Patent No.: US 12,661,405 B2
(45) Date of Patent: Jun. 23, 2026

(54) PROTECTED HDAC (HISTONE DEACETYLASE) INHIBITORS

(71) Applicant: LIGHTOX LIMITED, Wynyard Billingham Durham (GB)

(72) Inventors: Andrew Whiting, Wynyard Billingham Durham (GB); David Chisholm, Wynyard Billingham Durham (GB); Alba Pujol, Wynyard Billingham Durham (GB)

( * ) Notice: Subject to any disclaimer, the term of this patent is extended or adjusted under 35 U.S.C. 154(b) by 297 days.

(21) Appl. No.: 18/261,949

(22) PCT Filed: Jan. 20, 2022

(86) PCT No.: PCT/GB2022/050157

§ 371 (c)(1),
(2) Date: Jul. 18, 2023

(87) PCT Pub. No.: WO2022/157499

PCT Pub. Date: Jul. 28, 2022

(65) Prior Publication Data

US 2024/0123072 A1 Apr. 18, 2024

(30) Foreign Application Priority Data

Jan. 20, 2021 (GB) ...................................... 2100776
Jan. 20, 2021 (GB) ...................................... 2100778

(51) Int. Cl.

| | |
|---|---|
| ***A61K 41/00*** | (2020.01) |
| ***C07D 307/54*** | (2006.01) |
| ***C07D 333/24*** | (2006.01) |
| ***C07D 405/06*** | (2006.01) |
| ***C07D 417/06*** | (2006.01) |
| ***C07D 417/14*** | (2006.01) |

(52) U.S. Cl.

CPC ........ *A61K 41/0057* (2013.01); *C07D 307/54* (2013.01); *C07D 333/24* (2013.01); *C07D 405/06* (2013.01); *C07D 417/06* (2013.01); *C07D 417/14* (2013.01)

(58) Field of Classification Search

CPC .................................................. A61K 41/0057

See application file for complete search history.

(56) References Cited

FOREIGN PATENT DOCUMENTS

| | | | |
|---|---|---|---|
| WO | 03/082288 | A1 | 10/2003 |
| WO | 2021/009506 | A1 | 1/2021 |

OTHER PUBLICATIONS

European Examination Report; European Patent Office; Feb. 26, 2025.

International Searching Report; European Patent Office; May 3, 2022.

Guo et al; Stem Cells and Development; Jan. 21, 2010.

*Primary Examiner* — Golam M Shameem

(74) *Attorney, Agent, or Firm* — Patshegen IP; Moshe Pinchas

(57) ABSTRACT

The invention relates to protected HDAC inhibitor compounds of formula I, in which Y, $Ar^1$, $Ar^2$, X, $R^1$ and $R^2$ are as defined herein. In aspects, the inventions relates to use of the compounds, and to methods of deprotecting the compounds.

16 Claims, 12 Drawing Sheets

47

85

86

87

88

27

88

93

96
99
100

100
88
101

103

93

PROTECTED HDAC (HISTONE DEACETYLASE) INHIBITORS

Acetylation/deacetylation of histones plays a significant role in the transcriptional regulation of eukaryotic cells. The acetylation status of histones and non-histone proteins is determined by histone deacetylases (HDACs) and histone acetyl-transferases (HATs). Histone deacetylases (HDACs) belong to a family of enzymes that remove acetyl groups from the ε-amino moiety of a lysine group on histone and non-histone proteins. HDAC inhibitors (HDACi) inhibit the activity of HDAC enzymes—due to the biological importance of HDACs, their inhibition has significant clinical implications, and HDAC inhibition has emerged as an important therapeutic strategy for the treatment of cancer, neurodegenerative diseases, inflammatory diseases, and neurological disorders, amongst others.

HDAC enzymes are classified based on their homology of accessory domains to yeast histone deacetylases, and are currently classified into four main groups:

- Class I, which includes HDAC1, -2, -3 and -8 are related to yeast RPD3 deacetylase;
- Class IIA, which includes HDAC4, -5, -7 and -9; Class IIB-6, and -10 are related to yeast Hda1 (histone deacetylase 1) gene;
- Class III (also known as sirtuins) are related to the Sir2 gene and include SIRT1-7;
- Class IV, which contains only HDAC11 has features of both Class I and II.

Typical HDAC inhibitors act exclusively on Class I, II and IV HDACs by binding to the zinc-containing catalytic domain of the HDACs. These HDAC inhibitors can be further classified based on the chemical moiety that binds to the zinc ion (with the exception of cyclic tetrapeptides which bind to the zinc ion with a thiol group). Examples include hydroxamic acids (or hydroxamates), such as trichostatin A; cyclic tetrapeptides (such as trapoxin B), and the depsipeptides; benzamides; electrophilic ketones, and aliphatic acid compounds such as phenylbutyrate and valproic acid.

Hydroxamic acids constitute the largest class of HDAC inhibitors.

Examples of hydroxamic acid-based HDAC inhibitors include vorinostat (suberoylanilide hydroxamic acid, SAHA), belinostat, panobinostat, givinostat, pracinostat, quisinostat and abexinostat.

While HDAC inhibitors have an important therapeutic role, the instability of HDAC inhibitors such as hydroxamic acids causes difficulty in terms of shelf stability, solubility, formulation and manufacture etc.

It is an aim of the invention to address or mitigate one or more of these problems. It is an aim of this invention to provide protected HDAC inhibitors, and in particular protected hydroxamic acids. It is an aim of this invention to provide a protected HDAC inhibitor which may exhibit improved stability. It is an aim of this invention to provide a protected HDAC inhibitor which may exhibit improved solubility. Embodiments of the invention relate to methods of protecting and/or deprotecting HDAC inhibitors, such as hydroxamic acid-based HDAC inhibitors. In embodiments, the deprotecting step may be carried out in situ within cells and tissues, i.e. by endogenous enzymes.

SUMMARY OF THE INVENTION

The invention relates to the use of an ester as a protecting group. The invention relates to the use of an ester as a protecting group for a HDAC inhibitor. In this process, the functional group of the HDAC inhibitor, such as the hydroxamic group, is protected as an ester. The ester can then be removed in the presence of an enzyme. The enzyme may be an endogenous enzyme. The removal of the ester results in deprotection of the functional group. This deprotection may occur in situ, i.e. the enzyme may be an endogenous enzyme, and the deprotection may occur when the HDAC inhibitor enters cells. The cells may be mammalian cells. In embodiments, deprotection occurs when the HDAC inhibitor enters target cells, via action of an endogenous enzyme on the protecting ester group. This can result in in situ "clean" activation of HDAC inhibition.

The invention therefore encompasses a protected HDAC inhibitor. The protected HDAC inhibitor may be protected by an ester group. This may act as a pro-drug. It may function as an in-situ deprotectable HDAC inhibitor. In this embodiment, the protected HDAC inhibitor is metabolised to its active form after administration. This has significant advantages in terms of storage, formulation and manufacture etc. As used herein, the term "prodrug" means a compound or compounds that is administered in an inactive form, and which is converted to its active form in vivo via a chemical, biochemical or physiological process.

Advantageously, the ester can be selected to allow activation of HDAC inhibition only in target tissues through enzymatic removal, that is, the protecting group can be selected so that enzymatic removal occurs only in those cells, tissues or areas of the body of interest, i.e. those cells, tissues or areas of the body containing a complementary enzyme. The protecting group can further be tuned to modulate characteristics such as half-life, solubility, targeting etc, to suit the characteristics of the target tissue, as would be understood by one skilled in the art.

Suitable protecting groups include, but are not limited to: acetate (C1-C9) esters, hydroxyacetate (C1-C9) esters, methoxyacetate (C1-C9) esters, phenylacetate, propionate, butyrate, salicylate, pyruvate, lactate esters, citrate esters, PEG esters, glycerol esters, peptide esters e.g. mono-, di- and triglycine esters, phosphate esters, sulfonate esters, carbonates e.g. tetraethylene glycol, O-glycosyl ethers, O-glycosyl esters.

In an embodiment, the protecting group is an acetate (C1-C9) ester. In an embodiment, the protecting group is an acetate C1 ester.

Suitable enzymes for deprotection include, but are not limited to lipases, lactases, esterases, amylases, cytochrome P450s, glycosidases e.g. beta-glucoronidases, sucrases and hyaluronidases, peptidases, phosphatases and sulfatases.

In an embodiment, the enzyme is a lipase or a lactase.

In an embodiment, the HDAC inhibitor is a photoactive HDAC inhibitor, although the invention is not limited thereto, and it would be understood that the invention is more broadly applicable to HDAC inhibitors and HDAC inhibitor drugs.

In an embodiment, the HDAC inhibitor is a photoactive HDAC inhibitor. By "photoactive HDAC inhibitor" is meant a HDAC inhibitor which possesses dual cell modulatory activities, i.e. light-activated cell killing alongside HDAC inhibition activities such as biochemical influence and/or targeting.

An exemplary form of such a compound is shown below:

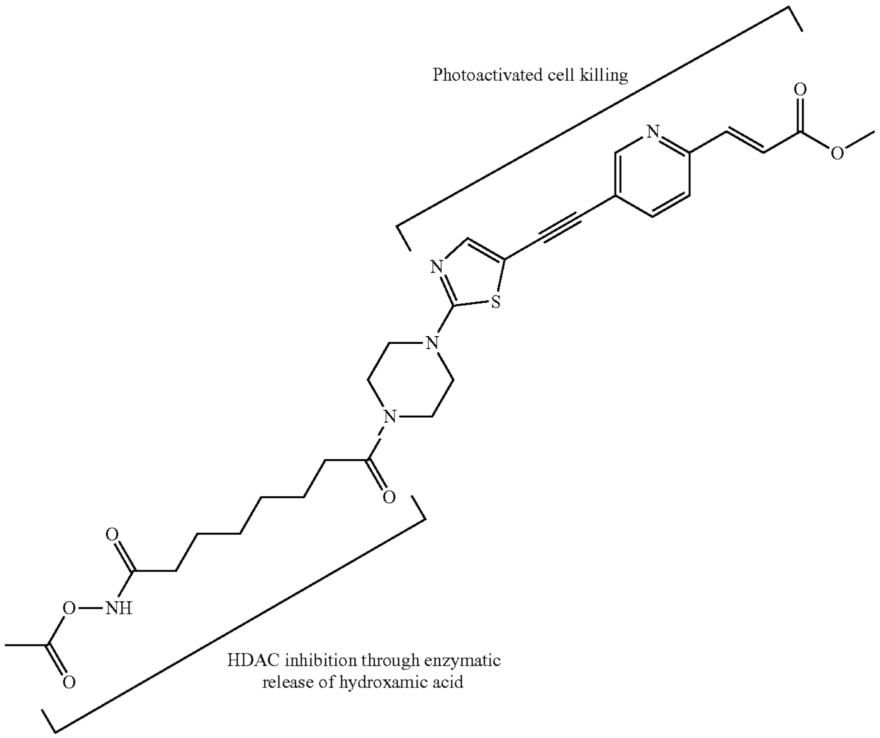 [SMILES: COC(=O)/C=C/c1ccc(C#Cc2cnc(N3CCN(C(=O)CCCCCCC(=O)NOC(C)=O)CC3)s2)cn1]

Examples of such HDAC inhibitors are compounds are disclosed herein. The inventors have demonstrated that when such photoactive HDAC inhibitors are protected according to the invention, cell-killing functionality is maintained. It has been observed that biological activity is delayed while deprotection takes place.

In an aspect of the invention there is provided a compound of formula I:

Formula 1

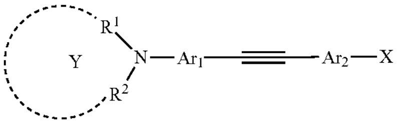

in which:

$R^1$ is H or an alkyl group comprising 1 to 10 carbon atoms;

$R^2$ is P—Z, in which P is an alkyl group comprising from 1 to 15 carbon atoms, optionally substituted with one or more of N atoms, —C═O, and —NHC═O;

and Z is:

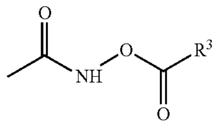

in which $R^3$ is H, a $C_1$-$C_9$ alkyl, —$CH_2OH$, —$CH_2OCH_3$, -Ph, —$C_6H_4OH$, —$CH(CH_3)OH$, —$C(CH_2COOH)_2OH$, —$C(=O)CH_3$, —$CH_2NH_2$, —$CH_2NH(C=O)CH_2NH_2$, or —$CH_2NH(C=O)CH_2NH(C=O)CH_2NH_2$;

Or $R^1$ and $R^2$ form part of a heterocyclic group Y having 5 or 6 members and being substituted with P-Z, wherein P is as defined above, and wherein Z is as defined above;

$Ar_1$ and $Ar_2$ are each, independently, selected from a phenyl, pyridine, pyrimidine, thiophene, furan, benzofuran or thiazole group; and X is —C═C—C(═O)$OR^4$, in which $R^4$ is an alkyl group comprising from 1 to 10 carbon atoms, optionally substituted with one or more 0 atoms.

The compounds of the invention have the general structure shown in Formula I above.

The term heterocyclic group having 5 or 6 members means a monocyclic ring group containing 5 or 6 ring members and optionally containing one or more heteroatoms selected from the group consisting of N, S, SO, $SO_2$, $O_2$ and O, in addition to the formula I Nitrogen atom. The term "heterocyclic group" includes aromatic, partially unsaturated and saturated ring systems. Examples of non-aromatic groups include piperazinyl, morpholinyl, thiomorpholinyl, dioxidothiomorpholinyl, pyrrolidin-1-yl, and pyrrolidin-3-yl groups but are not limited thereto. Examples of aromatic (heteroaryl) groups include pyrrolyl, imidazolyl, pyrazolyl, pyridinyl, pyrimidinyl, indolyl and benzothiadiazolyl groups, but are not limited thereto. In an embodiment, the heterocyclic group is a saturated ring system. According to formula I, the ring system is substituted with P-Z. In an embodiment, P—Z is in the 4-position relative to the formula I Nitrogen atom.

As used herein, the term "alkyl" refers to a fully saturated, branched, unbranched or cyclic hydrocarbon moiety, i.e. primary, secondary or tertiary alkyl, or where appropriate, cycloalkyl or alkyl substituted by cycloalkyl. Where not otherwise indicated, an alkyl group comprises from 1 to 10 carbon atoms, preferably from 1 to 6 carbon atoms, or more preferably 1 to 4 carbon atoms. Representative alkyl groups include, but are not limited to, methyl, ethyl, n-propyl, iso-propyl, n-butyl, sec-butyl, iso-butyl, tert-butyl, n-pentyl, iso-pentyl, neo-pentyl, n-hexyl, 3-methylhexyl; 2,2-dimethylpentyl; 2,3-dimethylpentyl, n-heptyl, n-octyl, n-nonyl and n-decyl.

In an embodiment, $R^3$ is a $C_1$-$C_6$ alkyl.

In an embodiment, $R_3$ is a $C_1$-$C_3$ alkyl. In an embodiment, $R_3$ is —$CH_3$.

In an embodiment, $Ar^1$ is a thiazole or phenyl group.

In an embodiment, $Ar^2$ is a pyridine, thiophene, or furan group.

In an embodiment, Ar1 is selected from a thiazole or phenyl group and $Ar^2$ is selected from a pyridine, thiophene, or furan group.

In an embodiment, $R^1$ and $R^2$ form part of a heterocyclic group Y. The heterocyclic group Y is substituted with P-Z, where P is an alkyl group comprising from 1 to 15 carbon atoms, optionally substituted with one or more of N atoms, —C═O, and —NHC═O;

and Z is:

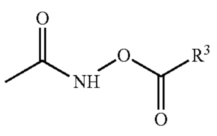

in which $R^3$ is H, a $C_1$-$C_9$ alkyl, —$CH_2OH$, —$CH_2OCH_3$, -Ph, —$C_6H_4OH$, —$CH(CH_3)OH$, —$C(CH_2COOH)_2OH$, —C(═O)$CH_3$, —$CH_2NH_2$, —$CH_2NH$(C═O)$CH_2NH_2$, or —$CH_2NH$(C═O)$CH_2NH$(C═O)$CH_2NH_2$.

In an embodiment, the substituent P-Z is in the 4-position relative to the formula I Nitrogen atom.

In an embodiment in which $R^1$ and $R^2$ form part of a heterocyclic group Y, Y is piperazine.

Y may be:

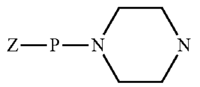

When Y is piperazine, P may be a $C_1$-$C_{15}$ alkyl group substituted with —C(═O). In an embodiment, P is —C(═O)$(CH_2)_6$.

In formula I, X is —C═C—C(═O)$OR^4$, in which $R^4$ is an alkyl group comprising from 1 to 10 carbon atoms, optionally substituted with one or more 0 atoms.

In an embodiment, $R^4$ is a $C_1$-$C_6$ alkyl group.

In an embodiment, $R^4$ is —$CH_3$, —$C(CH_3)_3$ or —$CH_2CH(CH_3)_2$.

Optionally, $R^1$ and $R^2$ do not form a heterocyclic group Y. In this embodiment, $R^1$ is H or an alkyl group comprising 1 to 10 carbon atoms; and $R^2$ is P—Z, in which P is an alkyl group comprising from 1 to 15 carbon atoms, optionally substituted with one or more of N atoms, —C═O, and —NHC═O;

and Z is:

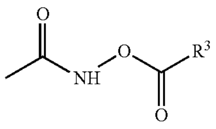

in which $R^3$ is H, a $C_1$-$C_9$ alkyl, —$CH_2OH$, —$CH_2OCH_3$, -Ph, —$C_6H_4OH$, —$CH(CH_3)OH$, —$C(CH_2COOH)_2OH$, —C(═O)$CH_3$, —$CH_2NH_2$, —$CH_2NH$(C═O)$CH_2NH_2$, or —$CH_2NH$(C═O)$CH_2NH$(C═O)$CH_2NH_2$. In this embodiment, $R^1$ may be a $C_1$-$C_3$ alkyl. In an embodiment, $R^1$ is —$CH_3$.

When $R^2$ is P—Z, P may be a $C_1$-$C_{15}$ alkyl substituted with —NHC(═O).

In an embodiment, P is —$(CH_2)_5$NHC(═O)$(CH_2)_6$.

In an embodiment, $R^4$ is —$(CH_2CH_2O)_nCH_3$ in which n is an integer between 1 and 8. In an embodiment, $R^4$ is —$(CH_2CH_2O)_3CH_3$.

In an embodiment, $R^4$ is —$(CH_2CH_2O)_nCH_3$ in which n is an integer between 1 and 8, preferably $R^4$ is —$(CH_2CH_2O)_3CH_3$, and $R^1$ and $R^2$ do not form a heterocyclic group.

In an embodiment, the compound of formula I is selected from compounds 92, 93, 101 and 102:

92
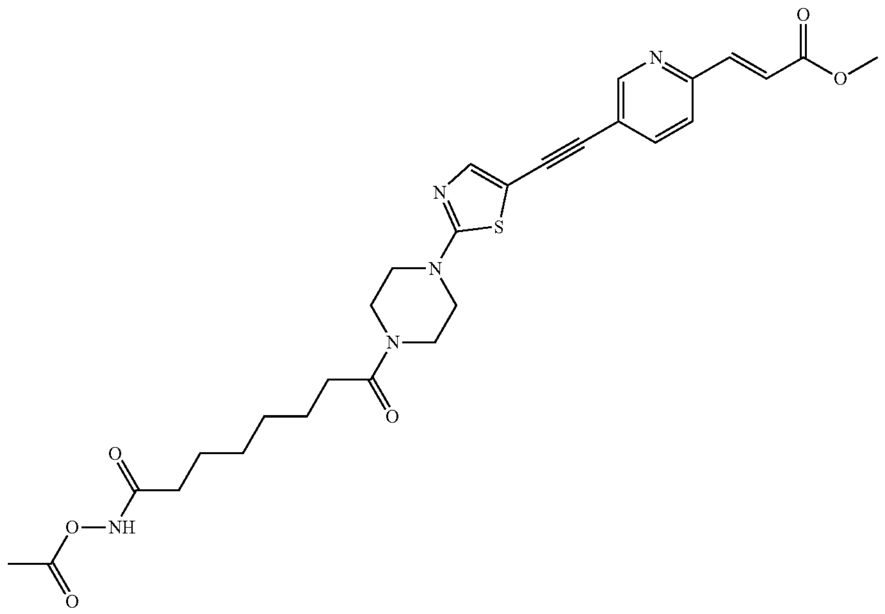
93
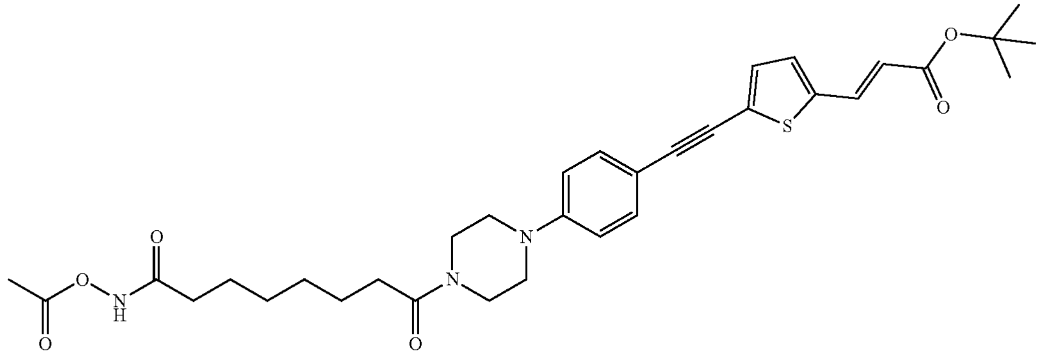
101
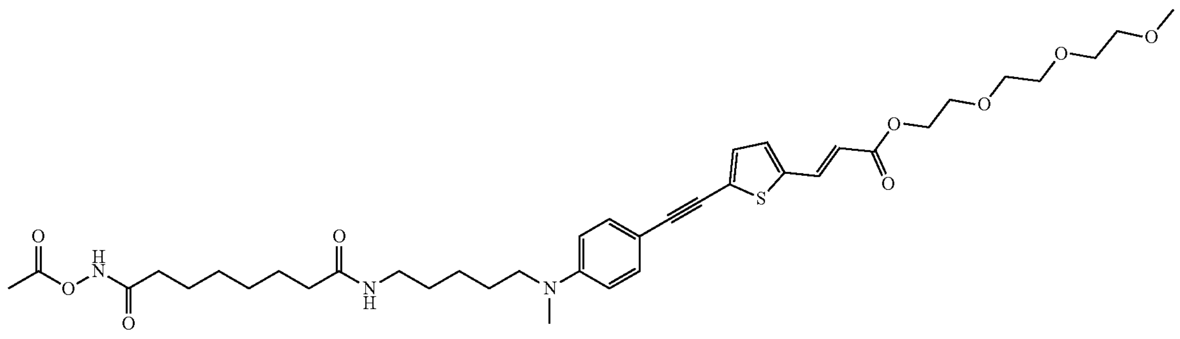

-continued

102

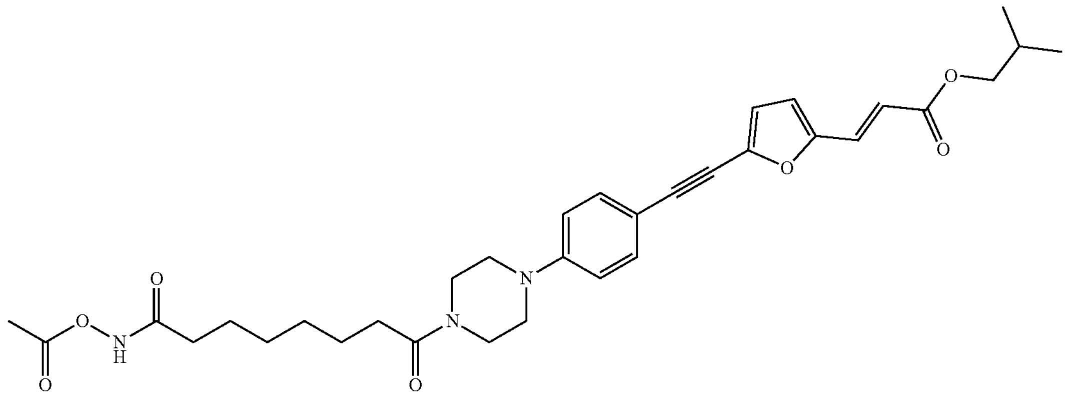

The compounds according to the present invention are inherently fluorescent. According to the invention the compounds may be used in fluorescence imaging.

In aspects, the invention relates to the use of the compounds of formula I in the generation of reactive oxygen species (ROS) when said compound is activated by light.

Triplet state photosensitizers (PS) typically comprise a light-harvesting region, which is responsible for the dual-functionality of light-harvesting and intersystem crossing, where electrons in the single state non-radiatively pass to the triplet state. Quenching of the triplet-excited state can result in the formation of reactive oxygen species (ROS), radicals from ground state molecular oxygen, or direct chemical reactions with surrounding molecules.

Localised ROS production is an immune defence strategy employed in both animal and plant systems in response to pathogen attack. Within animal, plant, fungal and bacterial cells, the ROS elicit a variety of modulatory effects depending on the rate and extent of their production; at high concentrations apoptosis is observed, while at low concentrations a stimulatory response is often observed (Guo et al. Stem Cells Dev. 2010, 19, 1321-1331).

Photodynamic therapy (PDT) exploits the ability of photosensitizers to generate ROS, typically to destroy cancer cells, pathogenic microbes and/or unwanted tissue by apoptosis. Typically, the photosensitizing compound is excited near/inside a particular target tissue or condition (e.g. microbial infections, neoplasias, tumours etc) causing the generation of large quantities of ROS and subsequent destruction of that tissue. At low levels of ROS, cell proliferation can be triggered, leading to applications in wound healing or more general tissue regeneration therapies.

Thus, PDT relies on the targeting of the photosensitive compound to accumulate in the desired location, such as the cells of the diseased tissue, and localised light delivery to activate ROS generation. While compounds for use in PDT are known, they often suffer from a variety of disadvantages, including small absorbance peaks, causing difficulties in light activation, particularly for bulky tumours where light penetration can be difficult to achieve; long biological half-lives, leading to skin photosensitivity for extended periods post-treatment; poor pharmacological properties such as poor aqueous solubility; and poor targeting ability (i.e. poor ability to target and accumulate in specific tissues or cells, leading to significant off-target damage).

Advantageously, the compounds of the present invention are biologically inert in the unactivated state, but generate ROS when irradiated with low to medium energy short-wavelength visible light.

The compounds of formula I can therefore be used to generate reactive oxygen species (ROS) and thereby control cellular development, i.e. to control proliferation, differentiation and apoptosis of cells, leading to a variety of therapeutic and non-therapeutic uses. The compounds of formula I are particularly advantageous for use in applications mediated by the control of ROS, as they demonstrate efficient targeting, which can lead to fewer off-target effects. They can also be tuned to different cell types, allowing selective targeting effects to be achieved.

In aspects, therefore, the invention relates to the use of the compounds or conjugates of the invention in photodynamic therapy (PDT).

The generation of ROS can be controlled based on the therapeutic need, for instance, to induce apoptosis for the ablation of cells, to cause proliferation in wound healing, or by a combination of these. For instance in wound care, high levels of ROS could initially be triggered, leading to apoptosis of bacterial and/or fungal cells, followed by low levels of ROS to aid in skin regeneration.

The invention therefore relates to a method of treatment of a patient with a disease or condition that benefits from HDAC inhibition, the method comprising administering to a patient a therapeutically effective amount of a compound of formula I or a conjugate thereof, wherein the compound of formula I is metabolised to its active form in vivo.

In an aspect, the invention relates to pharmaceutical composition comprising a compound of formula I, optionally in combination with one or more pharmaceutically acceptable excipients, diluents or carriers.

Advantageously, the compounds of formula I are protected as an ester, which imparts stability on the compounds. The protected compounds are more easily stored. The protected compounds may exhibit improved solubility. Activation of the compound involves removal of the protecting group.

An aspect of the invention relates to a method of deprotecting a compound of formula I, the method comprising bringing the compound of formula I into contact with an enzyme.

The enzyme may be an endogenous enzyme. Suitable enzymes for deprotection include, but are not limited to lipases, lactases, esterases, amylases, cytochrome P450s, glycosidases e.g. beta-glucoronidases, sucrases and hyaluronidases, peptidases, phosphatases, sulfatases.

In an embodiment, the enzyme is a lipase or a lactase.

Advantageously, the ester protecting group can be selected to allow activation of HDAC inhibition only in target tissues through enzymatic removal, that is, the protecting group can be selected so that enzymatic removal occurs only in those cells, tissues or areas of the body of interest, i.e. those cells, tissues or areas of the body containing a complementary enzyme.

The protecting group can further be tuned to modulate characteristics such as half-life, solubility, targeting etc, to suit the characteristics of the target tissue, as would be understood by one skilled in the art.

Suitable protecting groups include, but are not limited to: acetate (C1-C9) esters, hydroxyacetate (C1-C9) esters, methoxyacetate (C1-C9) esters, phenylacetate, propionate, butyrate, salicylate, pyruvate, lactate esters, citrate esters, PEG esters, glycerol esters, peptide esters e.g. mono-, di- and triglycine esters, phosphate esters, sulfonate esters, carbonates e.g. tetraethylene glycol, O-glycosyl ethers, O-glycosyl esters.

In an embodiment, the protecting group is an acetate (C1-C9) ester. When the ester protecting group is a C1 acetate ester, $R^3$ in the compound of formula I is —$CH_3$.

According to an aspect of the present invention there is provided a method of deprotecting a compound of formula I, the method comprising reacting a compound of formula I with a base in the presence of a solvent.

Suitable bases for use in the method of the invention include NaOH, LiOH, KOH, $Li_2CO_3$, $Na_2CO_3$, $K_2CO_3$, $Cs_2CO_3$, LiOMe, NaOMe, KOMe, LiOEt, NaOEt, KOEt, $LiO^tBu$ and $KO^tBu$.

The solvent may be a polar solvent. Suitable solvents include methanol, ethanol, propanol, butanol n-alcohols, iso-propanol, iso-butanol, sec-butanol, tert-butanol, water, tetrahydrofuran, 1,4-dioxane, acetonitrile, N,N-dimethylformamide, N,N-dimethylacetamide and dimethylsulfoxide.

The method can be carried out at from 5° C. to 100° C., or from 15° C. to 30° C. Advantageously, the method can be carried out at room temperature.

The reaction can be carried out for from 30 minutes to 48 hours. In an embodiment, the reaction is carried out at from 1 hour to 12 hours, or from 2 hours to 7 hours.

Once the reaction has taken place, the reaction mixture can be worked up using techniques known to one skilled in the art. For example, the reaction mixture can be diluted and the combined organics washed and dried and evaporated to give the deprotected compound as a crude solid.

The invention therefore relates to protected HDAC inhibitors, examples of which include the following compounds:

92

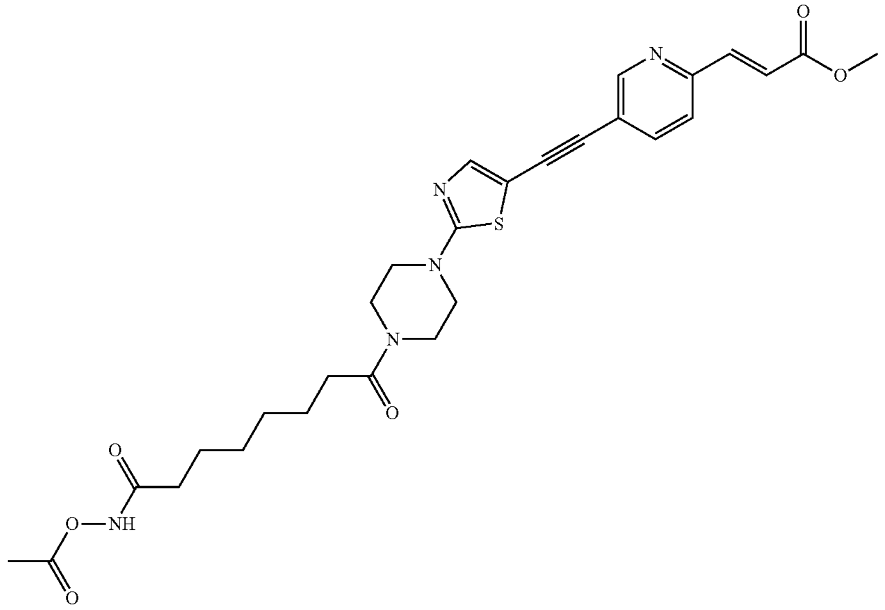

93

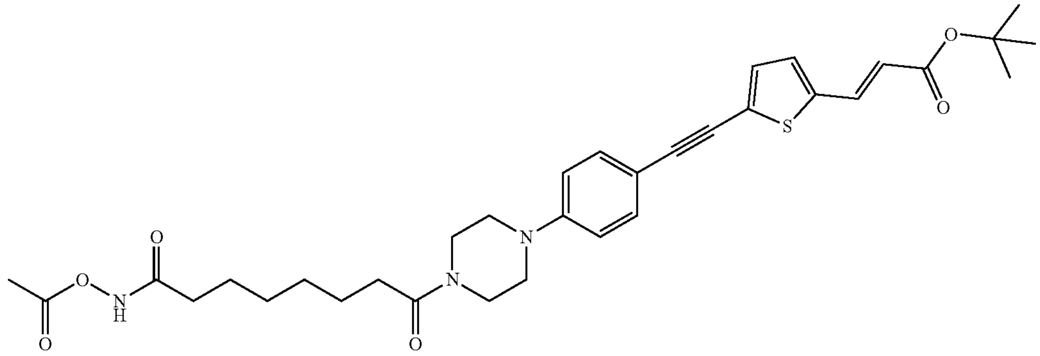

-continued

101

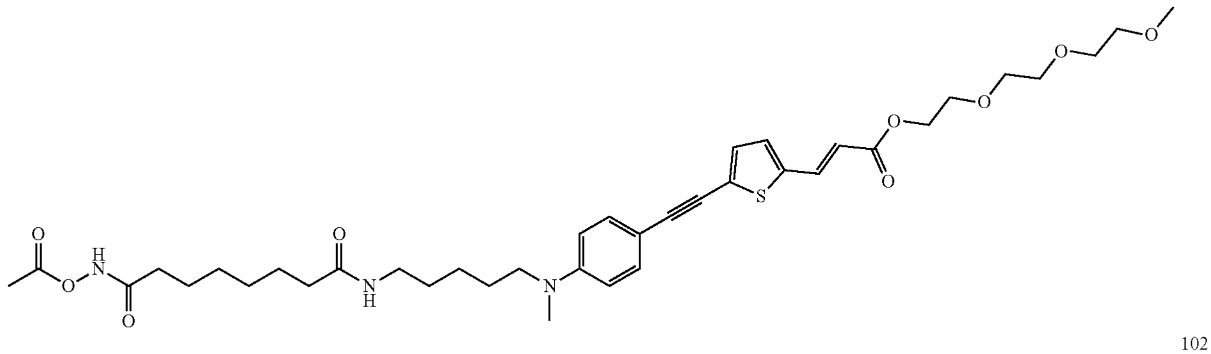

102

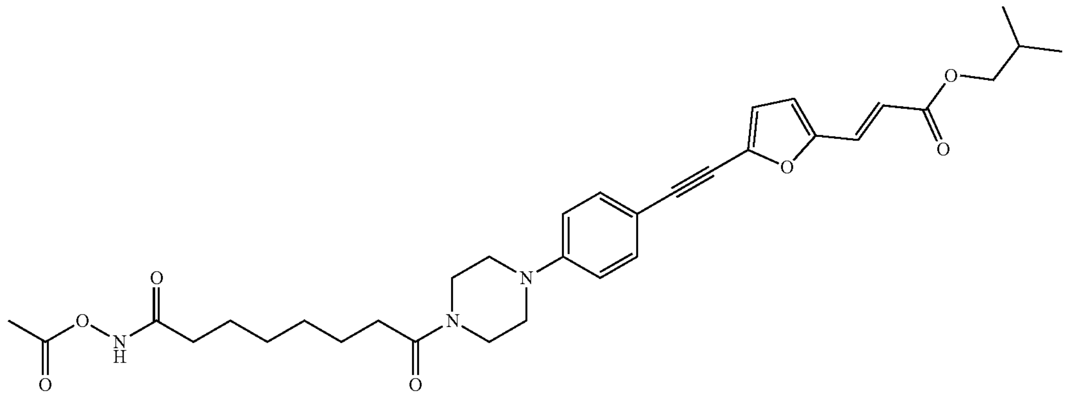

In an embodiment, the protected HDAC inhibitor is compound 92, compound 93, compound 101 or compound 102.

In an embodiment, the protected HDAC inhibitor is compound 92, compound 93 or compound 101.

Related compounds, useful as control compounds, include compounds 12, 13 and 14 below:

12

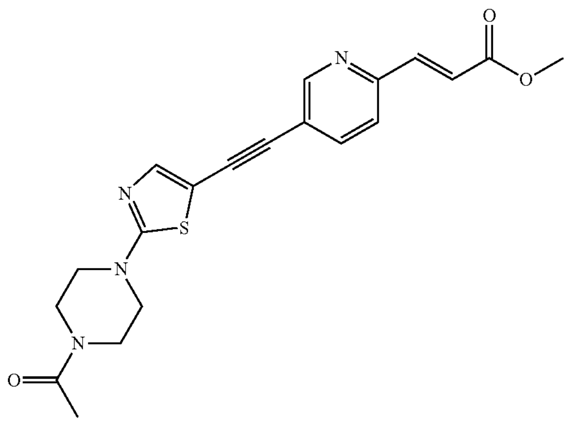

-continued

13

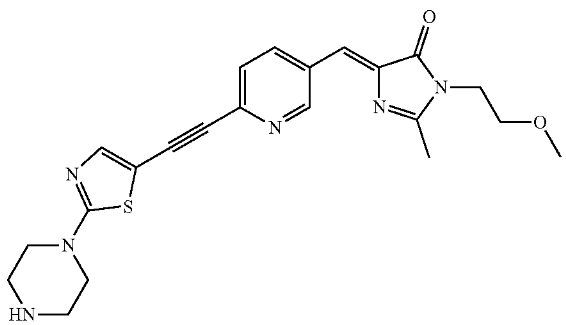

14

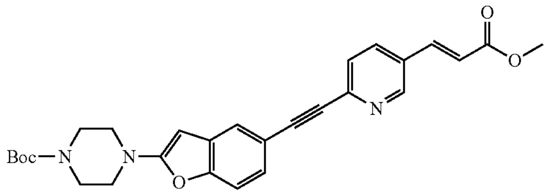

An aspect of the invention relates to a method of deprotecting a compound of formula I, the method comprising reacting a compound of formula I with a base in the presence of a solvent.

The method optionally comprises a purification step.

The invention relates to a method of protecting a HDAC inhibitor as an ester and removing the ester with an esterase to activate HDAC inhibition. The esterase may be an endogenous esterase. Removing the ester with an esterase may be carried out in vivo.

The invention relates to a method of treatment of a disorder or condition which is mediated by HDAC inhibition, the method comprising administering a protected HDAC inhibitor as herein described, wherein the HDAC inhibitor is subsequently deprotected in situ.

The compound of formula I may advantageously exhibit increased solubility, improved chemical and shelf stability and ease of manufacture compared with its deprotected counterpart (FIG. 1).

EXAMPLES

The invention will now be described by way of example only with reference to the accompanying figures, in which.

Figure 12:
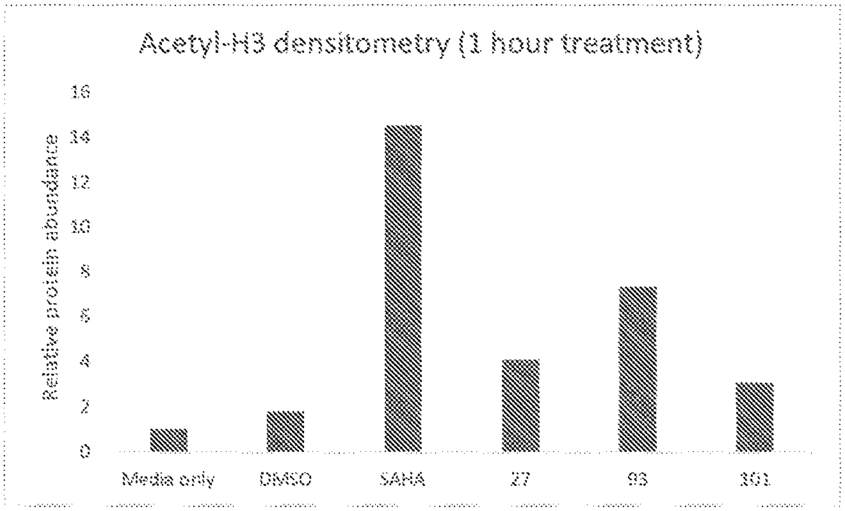
Figure 13:
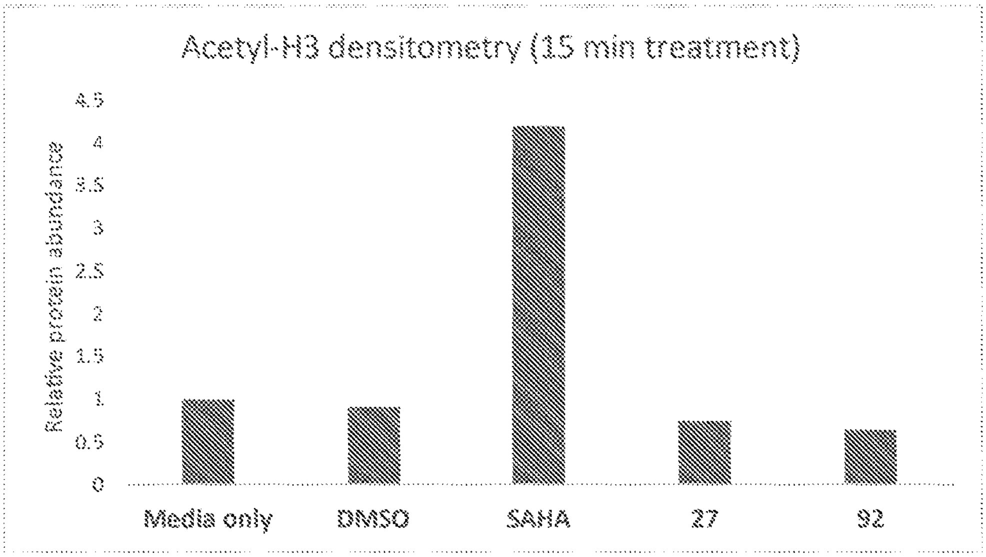
Figure 14:
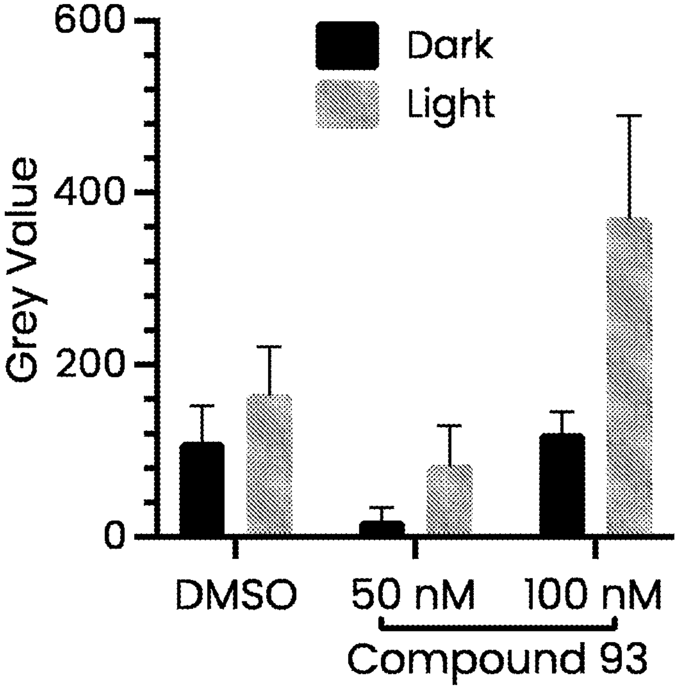
Figure 15:
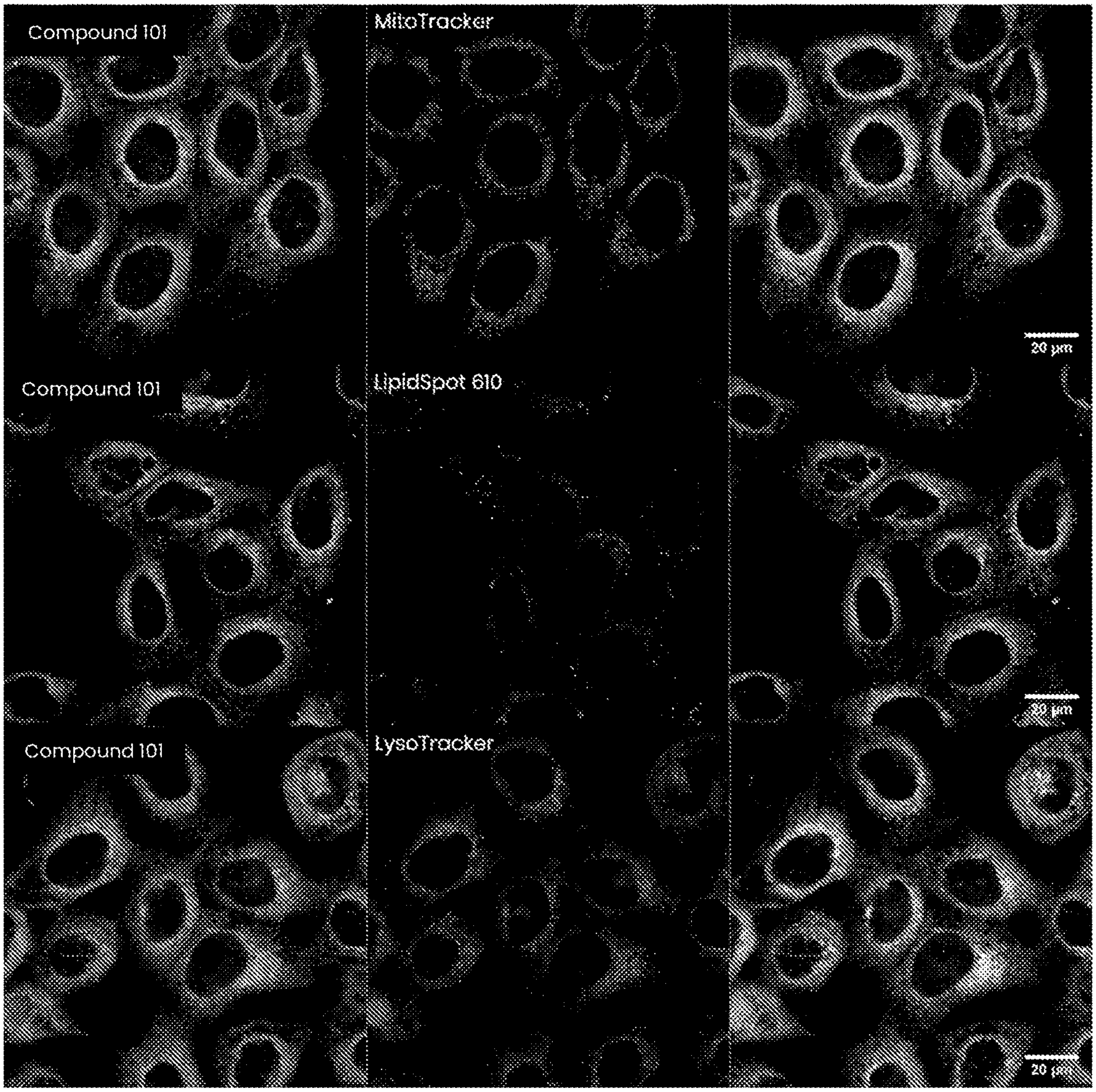
Figure 16:
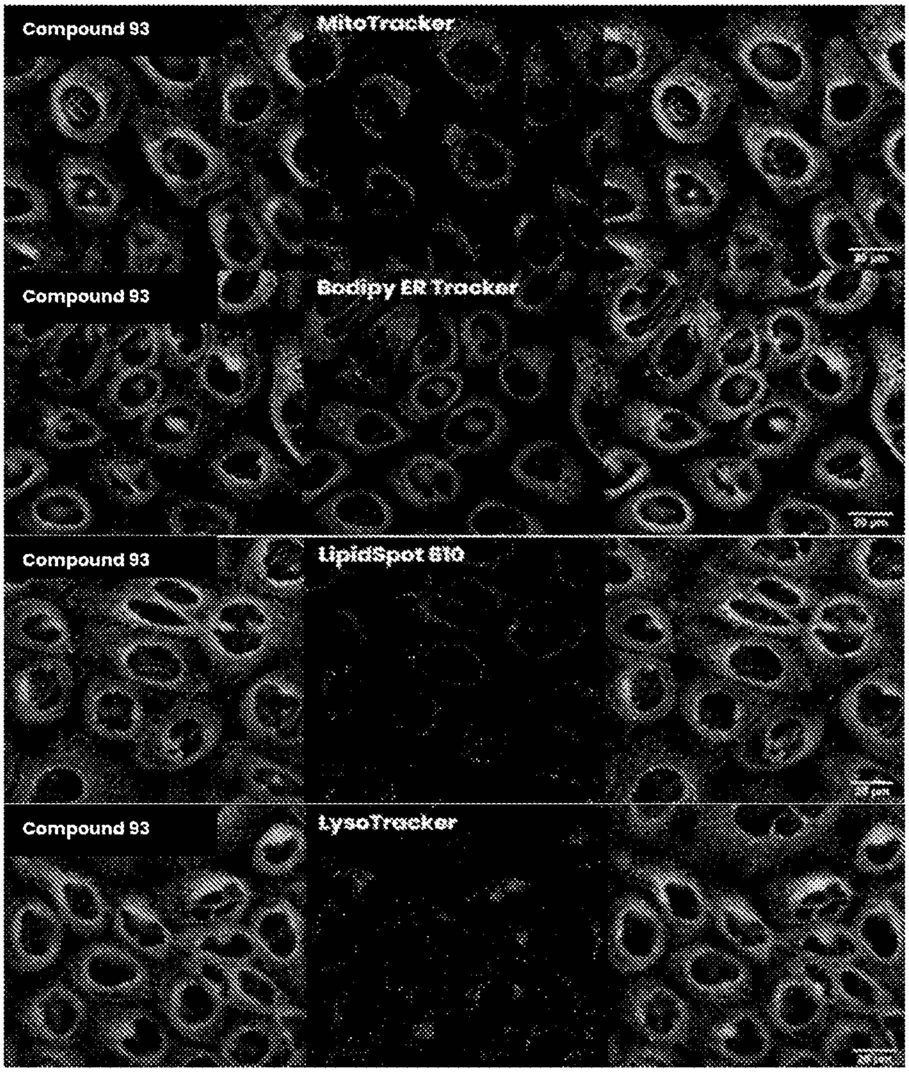
Figure 17:
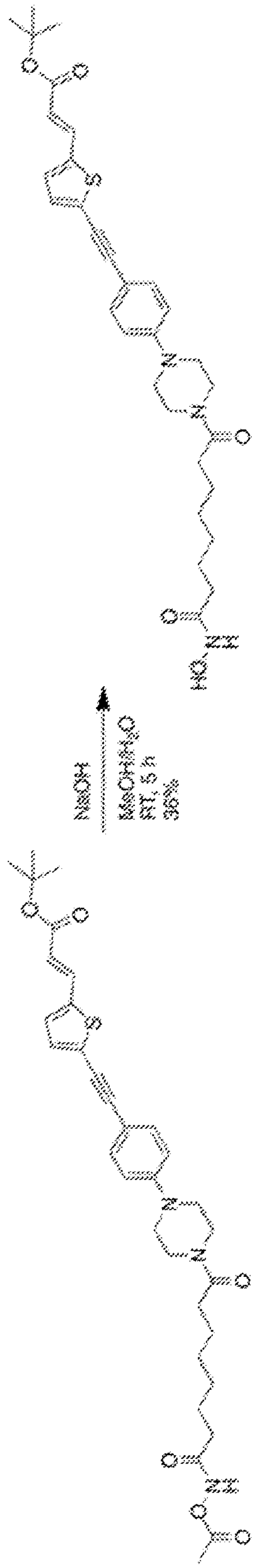

FIG. 12 shows the abundance of acetyl-H3 in SCC-4 cells in response to treatment after 1 hour with compound 93 and compound 101 according to the invention, and with control compounds;

FIG. 13 shows the abundance of acetyl-H3 in SCC-4 cells in response to treatment after 15 minutes with compound 92 according to the invention, and with control compounds;

FIG. 14 shows expression levels of caspase-3 in HaCaT cells after treatment with 50 nM compound 93 and 100 nM compound 93 before and after light activation, versus controls;

FIG. 15 shows fluorescence microscopy images demonstrating co-localisation of compound 101;

FIG. 16 shows fluorescence microscopy images demonstrating co-localisation of compound 93;

FIG. 17 shows the exemplary deprotection of compound 93.

EXPERIMENTAL EXAMPLES

General Methodology

All light irradiation was carried out using a modified PhotoReact 365™ which emits light at 405 nm with a power of 29 $mW/cm^2$ over 5 minutes. All image analysis was performed using ImageJ software and all graphs were made using Prism.

Cell Viability Assays:

Opaque-walled 96-well plates were seeded with 20,000 SCC-4 cells per well. The next day, plates were treated with the compound of interest at a range of concentrations (100 pM-1 pM) for 1 hour before irradiation of the "Light" treated plates. The following day, plates were treated with either:

- propidium iodide (PI) and fluorescein diacetate (FDA) for 10 minutes then washed in PBS before fluorescence was measured at 535/617 nm for PI and 485/520 nm for FDA.
- 12 mM MTT (3-(4,5-Dimethylthiazol-2-yl)-2,5-diphenyltetrazolium bromide) solution for 2 hours before lysing in DMSO on an orbital shaker and measuring absorbance at 540 nm.
- XTT (2,3-Bis-(2-Methoxy-4-Nitro-S-Sulfophenyl)-2H-Tetrazolium-5-Carboxanilide) labelling reagent and electron coupling reagent for 4 hours before washing with PBS and measuring absorbance at 650 nm.
- CellTitre-Glo™ reagent for 10 minutes on an orbital shaker to lyse cells before measuring luminescence.

Microscopy Procedures:

Co-Localisation

SCC-4 cells were seeded at 50,000 cells per well on 8-well chamber slides and the following day were treated with 1 pM compound of interest for 1 hour before either fixation with 4% paraformaldehyde (PFA) or a media change to Live Cell Imaging solution. Co-stains (e.g. MitoTracker, Bodipy ER Tracker or LipidSpot 610) were applied for 30 minutes before imaging on a Zeiss LSCM 880.

Immunofluorescence

HaCaT or SCC-4 cells were seeded at 50,000 cells per well in sterile coverslip containing 6-well plates. The next day, cells were treated with the compound of interest for 30 minutes before "Light" treated cells were irradiated. The following day, cells were then fixed using 4% PFA, permeabilised using Triton X-100/Tween 20, blocked in BSA/goat serum (dependent on the antibodies) and stained with primary then secondary antibodies before coverslips were mounted on slides and imaged on a Zeiss LSCM 880.

Immunoprecipitation

SCC-4 cells were seeded at 350,000 cells per well of a 6-well plate and the following day, cells were treated with the compound of interest. After the required incubation, "Light" treated cells were irradiated and all cells were lysed using RIPA buffer. SDS-PAGE was performed and proteins transferred onto a nitrocellulose/PVDF membrane before blocking and primary then secondary antibody staining. Chemiluminescence signal was imaged using an iBright Imaging System.

Example 1: Synthesis of Acetate-Protected Hydroxamic Acid, 88

Figure 1:
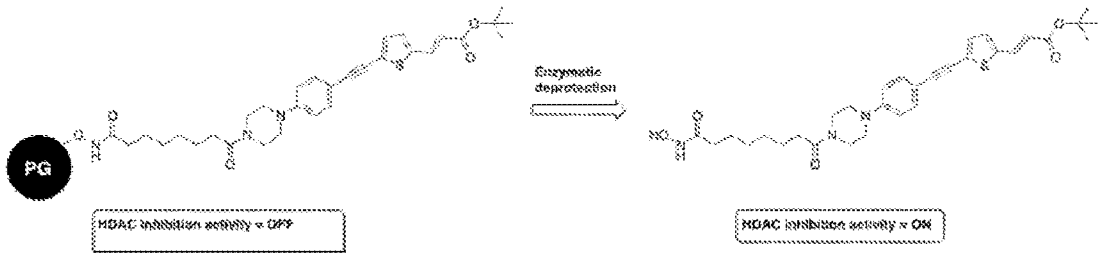
FIG. 1 shows a schematic of the invention, with PG indicating a protecting group.
Figure 2:
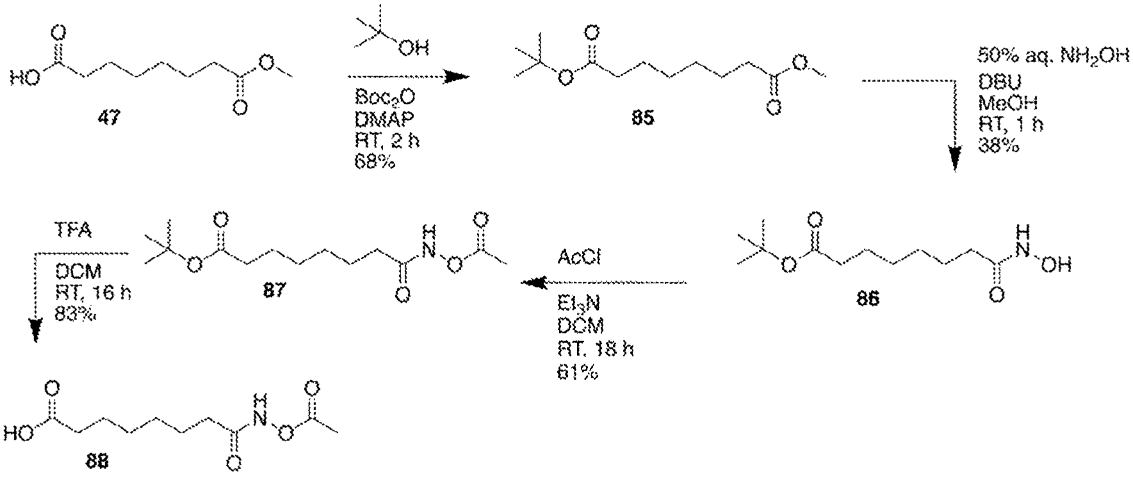
FIG. 2 shows the exemplary synthesis of acetate-protected hydroxamic acid (88)

The synthesis of an exemplary acetate-protected hydroxamic acid, 88, is shown in FIG. 2 and described further in examples 1.1 to 1.4 below.

Example 1.1

Synthesis of 1-Tert-butyl 8-methyl octanedioate, 85

Compound 47 (33.0 g, 175 mmol) was dissolved in tert-butanol (250 mL) and cooled to 0° C., whereupon di-tert-butyl dicarbonate (57.3 g, 262.5 mmol) and 4-dimethylaminopyridine (6.4 g, 52.5 mmol) were added and the resultant suspension was stirred rapidly at RT for 2 h. The solution was diluted with 5% HCl and extracted (3×) with dichloromethane (DCM). The organics were washed with sat. $NH_4Cl$ and $H_2O$, dried ($MgSO_4$) and evaporated to give a crude red oil (58.9 g). This was purified by $SiO_2$ chromatography (hexane/ethyl acetate (EtOAc)), 9:1) to give compound 85 as a colourless oil (29.06 g, 68%): $^1$H NMR (400 MHz, $CDCl_3$) δ 1.28-1.35 (m, 4H), 1.43 (s, 9H), 1.54-1.65 (m, 4H), 2.19 (t, J=7.5 Hz, 2H), 2.29 (t, J=7.5 Hz, 2H), 3.65 (s, 3H); $^{13}$C NMR (101 MHz, $CDCl_3$) δ 24.7, 24.9, 28.1, 28.7, 28.8, 34.0, 35.5, 51.4, 79.9, 173.1, 174.2.

Example 1.2

Synthesis of Tert-butyl 7-(hydroxycarbamoyl)heptanoate, 86

Compound 85 (6.1 g, 25.0 mmol) was dissolved in methanol (MeOH) (21 mL), whereupon 1,8-diazabicyclo [5.4.0]undec-7-ene (DBU) (11.2 mL, 75.0 mmol) and hydroxylamine ($NH_2OH$) (50% aq., 15.3 mL, 250 mmol) was added and the resultant solution was stirred at room temperature (RT) for 3 h. The mixture was diluted with dichloromethane (DCM) and the organics were washed with 5% HCl and $H_2O$, dried ($MgSO_4$) and evaporated to give a crude yellow oil (3.23 g). This was purified by $SiO_2$ chromatography (dichloromethane/methanol, 9:1) to give compound 86 as a colourless oil (2.34 g, 38%): 1H NMR (400 MHz, $CDCl_3$) δ 1.26-1.37 (m, 4H), 1.43 (s, 9H), 1.52-1.68 (m, 4H), 2.14 (s, 2H), 2.19 (t, J=6.9 Hz, 2H).

Example 1.3

Synthesis of Tert-butyl 7-[(acetyloxy)carbamoyl]heptanoate, 87

Compound 86 (2.3 g, 9.37 mmol) was dissolved in dichloromethane (40 mL) whereupon acetyl chloride (0.8 mL, 11.24 mmol) and triethylamine (1.56 mL, 11.24 mmol) were added, and the resultant solution was stirred at RT for 3 h. The solution was diluted with dichloromethane and the organics were washed with sat. $NH_4Cl$ and $H_2O$, dried ($MgSO_4$) and evaporated to g) give a crude light yellow oil (2.75 g). This was purified by $SiO_2$ chromatography (dichloromethane/methanol, 99:1) to give compound 87 as a colourless oil (1.65 g, 61%): $^1$H NMR (400 MHz, $CDCl_3$) δ 1.24-1.37 (m, 4H), 1.39 (s, 9H), 1.48-1.58 (m, 2H), 1.59-1.69 (m, 2H), 2.13-2.19 (m, 2H), 2.17 (s, 3H), 2.18-2.23 (m, 2H), 9.64 (s, 1H); $^{13}$C NMR (101 MHz, $CDCl_3$) δ 18.2, 24.7, 28.0, 28.4, 28.5, 32.6, 35.3, 80.1, 168.7, 173.3; MS(ES): m/z=288.2 $[M+H]^+$; HRMS (ES) calcd. for $C_{14}H_{26}NO_5$ $[M+H]^+$: 288.1805, found 288.1801.

Example 1.4

Synthesis of 7-[(Acetyloxy)carbamoyl]heptanoic acid, 88

Compound 87 (1.65 g, 5.74 mmol) was dissolved in dichloromethane (60 mL), whereupon trifluoroacetic acid (TFA) (5 mL, 65 mmol) was added and the resultant solution was stirred at room temperature for 18 h. The solution was evaporated, and the crude residue was purified by $SiO_2$ chromatography (dichloromethane/methanol, 95:5) to give compound 88 as a white solid (1.10 g, 83%): $^1$H NMR (700 MHz, DMSO-$d_6$) δ 1.23-1.28 (m, 4H), 1.45-1.52 (m, 4H), 2.09 (t, J=7.4 Hz, 2H), 2.13 (s, 3H), 2.18 (t, J=7.4 Hz, 2H), 11.53 (br, 1H), 11.95 (br, 1H); $^{13}$C NMR (176 MHz, DMSO-$d_6$) δ 18.1, 24.3, 24.6, 28.1, 28.2, 31.8, 33.6, 168.5, 169.7, 174.4; MS(ES): m/z=232.1 $[M+H]^+$; HRMS (ES) calcd. for $C_{10}H_{18}NO_5$ $[M+H]^+$: 232.1179, found 232.1167.

Example 2: Synthesis of Protected HDAC Inhibitor, 92

Figure 3:
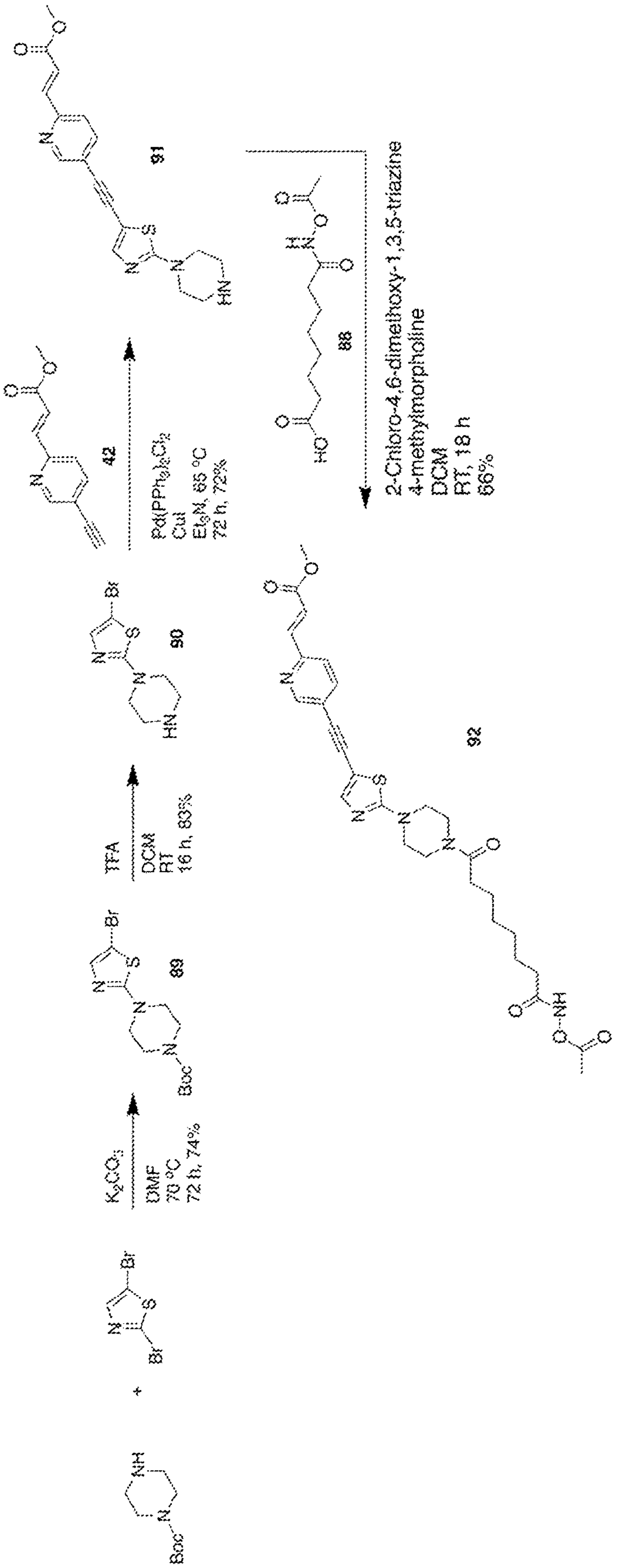
FIG. 3 shows the exemplary synthesis of a protected HDAC inhibitor with light-activated cell-killing activity according to the invention (92)

The synthesis of an exemplary protected HDAC inhibitor with light-activated cell-killing activity, 92, is shown in FIG. 3 and described further in examples 2.1 to 2.4 below.

Example 2.1

Synthesis of Tert-butyl 4-(5-bromo-1,3-thiazol-2-yl) piperazine-1-carboxylate, 89

2,5-Dibromo-1,3-thiazole (10 g, 41.2 mmol) was dissolved in N,N-dimethylformamide (DMF) (100 mL), whereupon 1-Boc-piperazine (10 g, 53.5 mmol) and $K_2CO_3$ (7.40 g, 53.5 mmol) were added and the resultant mixture was stirred at 70° C. for 72 h. The mixture was cooled, diluted with $H_2O$ and extracted with ethyl acetate. The organics were washed with $H_2O$ and brine, dried ($MgSO_4$) and evaporated to give a crude oil. This was purified by $SiO_2$ chromatography (petroleum ether/ethyl acetate, 8:2) to give compound 89 as a light yellow solid (10.5 g, 74%): $^1$H NMR (400 MHz, $CDCl_3$) δ 1.46 (s, 9H), 3.38-3.41 (m, 4H), 3.52-3.55 (m, 4H), 7.06 (s, 1H); $^{13}$C NMR (101 MHz, $CDCl_3$) δ 28.3, 48.0, 80.4, 95.2, 140.4, 154.5, 171.5.

Example 2.2

Synthesis of 1-(5-Bromo-1,3-thiazol-2-yl)piperazine, 90

Compound 89 (10.45 g, 30.0 mmol) was dissolved in dichloromethane (100 mL) whereupon trifluoracetic acid (9.2 mL, 120.0 mmol) was added and the resultant solution was stirred at RT overnight. The solution was evaporated to give a crude yellow oil (23 g). This was purified by $SiO_2$ chromatography (dichloromethane/methanol, 95:5) to give the trifluoroacetate salt of the desired compound (10.7 g). This was subsequently dissolved in dichloromethane and stirred rapidly with sat. $NaHCO_3$ for 0.5 h. The organics were washed with $H_2O$, dried ($MgSO_4$) and evaporated to give compound 90 as a white solid (6.15 g, 83%): $^1$H NMR (400 MHz, DMSO-$d_6$) δ 2.73-2.77 (m, 4H), 3.24-3.27 (m, 4H), 7.18 (s, 1H); MS(ES): m/z=248.0, 250.0 $[M+H]^+$; HRMS (ES) calcd for $C_7H_{11}N_3SBr$ $[M+H]^+$: 247.9852, found 247.9850.

Example 2.3

Synthesis of Methyl (2E)-3-(5-{2-[2-(piperazin-1-yl)-1,3-thiazol-5-yl]ethynyl}pyridin-2-yl)prop-2-enoate, 91

Triethylamine ($Et_3N$)(200 mL) was degassed by sparging with Ar for 1 h. Compound 90 (2.80 g, 11.3 mmol), compound 42 (2.32 g, 12.41 mmol), $Pd(PPh_3)_2Cl_2$ (390 mg, 0.18 mmol) and CuI (107 mg, 0.18 mmol) were then added under Ar and the resultant suspension was stirred at 60° C. for 72 h. The solvent was then evaporated to give a crude solid which was purified twice by $SiO_2$ chromatography (95:5 to 9:1, dichloromethane/methanol, 1% triethylamine) to give compound 91 as a bright orange solid (2.28 g, 57%): $^1H$ NMR (400 MHz, DMSO-$d_6$) δ 2.75-2.82 (m, 4H), 3.35-3.41 (m, 4H), 3.75 (s, 3H), 6.91 (d, J=15.7 Hz, 1H), 7.58 (s, 1H), 7.69 (d, J=15.7 Hz, 1H), 7.79 (dd, J=8.1, 0.9 Hz, 1H), 7.96 (dd, J=8.1, 2.2 Hz, 1H), 8.72 (dd, J=2.2, 0.9 Hz, 1H); MS (ES) m/z=355.1 $[M+H]^+$; HRMS (ES) calcd. for $C_{18}H_{19}N_4O_2S$ $[M+H]^+$: 355.1223, found 355.1223.

Example 2.4

Synthesis of Methyl (2E)-3-(5-{2-[2-(4-{7-[(acetyloxy)carbamoyl]heptanoyl}piperazin-1-yl)-1,3-thiazol-5-yl]ethynyl}pyridin-2-yl)prop-2-enoate, 92

Compound 88 (0.39 g, 1.69 mmol) and 2-chloro-4,6-dimethoxy-1,3,5-triazine (0.32 g, 1.85 mmol) was dissolved in dichloromethane (30 mL) at 0° C., whereupon 4-methylmorpholine (0.20 mL, 1.85 mmol) was added dropwise over 5 mins. The resultant mixture was stirred at 0° C. for 2 h whereupon compound 91 (0.5 g, 1.41 mmol) and 4-methylmorpholine (0.19 mL, 1.68 mmol) were added and the mixture was stirred for 18 h at RT. The mixture was diluted with dichloromethane, washed with $H_2O$, dried ($MgSO_4$) and evaporated to give a crude yellow solid (1.7 g). This was purified by $SiO_2$ chromatography (99:1, dichloromethane/methanol) and further recrystallised from acetonitrile (MeCN) to give compound 92 as a yellow solid (0.53 g, 66%): $^1H$ NMR (700 MHz, $CDCl_3$) δ 1.35-1.44 (m, 4H), 1.64-1.68 (m, 2H), 1.69-1.73 (m, 2H), 2.22 (s, 3H), 2.26 (t, J=7.4 Hz, 2H), 2.39 (t, J=7.4 Hz, 2H), 3.50 (t, J=5.4 Hz, 2H), 3.58-3.65 (m, 4H), 3.78 (t, J=5.4 Hz, 2H), 3.82 (s, 3H), 6.93 (d, J=15.6 Hz, 1H), 7.38 (dd, J=8.2, 0.9 Hz, 1H), 7.45 (s, 1H), 7.66 (d, J=15.6 Hz, 1H), 7.74 (dd, J=8.1, 2.1 Hz, 1H), 8.69 (dd, J=2.1, 0.8 Hz, 1H), 9.32 (s, 1H); $^{13}C$ NMR (176 MHz, $CDCl_3$) δ 18.3, 24.7, 28.1, 28.3, 32.5, 32.8, 40.6, 44.7, 48.0, 48.4, 51.9, 85.4, 91.2, 106.6, 120.7, 122.5, 123.5, 138.3, 142.7, 146.0, 151.3, 151.9, 167.1, 171.5, 171.8; MS(ES): m/z=568.2 $[M+H]^+$; HRMS (ES) calcd for $C_{28}H_{34}N_5O_6S$ $[M+H]^+$: 568.2224, found 568.2220.

Example 3: Synthesis of Protected HDAC Inhibitor, 93

Figure 4:
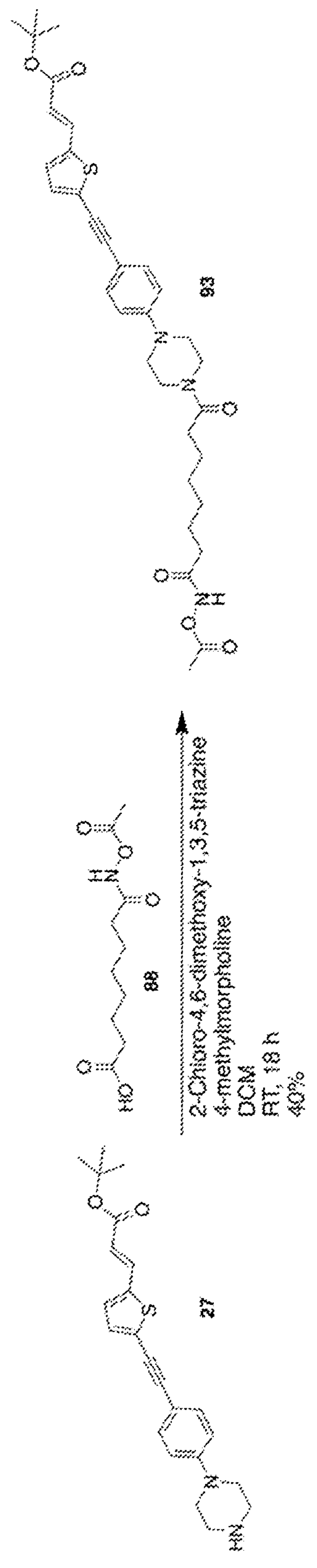
FIG. 4 shows the exemplary synthesis of an alternative protected HDAC inhibitor with light-activated cell-killing activity according to the invention (93)

The synthesis of Tert-butyl (2E)-3-(5-{2-[4-(4-{7-[(acetyloxy)carbamoyl]heptanoyl}piperazin-1-yl)phenyl]ethynyl}thiophen-2-yl)prop-2-enoate, 93 is shown in FIG. 4 and detailed below.

Compound 88 (2.89 g, 12.5 mmol) and 2-chloro-4,6-dimethoxy-1,3,5-triazine (2.39 g, 13.6 mmol) was dissolved in dichloromethane (100 mL) at 0° C., whereupon 4-methylmorpholine (1.5 mL, 13.6 mmol) was added dropwise over 5 mins. The resultant mixture was stirred at 0° C. for 2 h whereupon compound 27 (4.11 g, 10.41 mmol) and 4-methylmorpholine (1.36 mL, 12.4 mmol) were added and the mixture was stirred for 18 h at RT. The mixture was diluted with dichloromethane, washed with $H_2O$, dried ($MgSO_4$) and evaporated to give a crude yellow solid (1.7 g). This was purified by $SiO_2$ chromatography (97:3, dichloromethane/methanol) and further recrystallised from acetonitrile to give compound 93 as a yellow solid (2.51 g, 40%): $^1H$ NMR (600 MHz, $CDCl_3$) δ 1.32-1.45 (m, 4H), 1.50 (s, 9H), 1.63 (p, J=7.1 Hz, 2H), 1.69 (p, J=7.1 Hz, 2H), 2.19 (s, 3H), 2.25 (t, J=7.2 Hz, 2H), 2.37 (t, J=7.5 Hz, 2H), 3.21 (t, J=5.3 Hz, 2H), 3.24 (t, J=5.3 Hz, 2H), 3.55-3.66 (m, 2H), 3.75 (t, J=5.2 Hz, 2H), 6.11 (dd, J=15.6, 1.1 Hz, 1H), 6.84 (d, J=8.7 Hz, 2H), 7.03-7.14 (m, 2H), 7.36-7.44 (m, 2H), 7.58 (d, J=15.6 Hz, 1H), 9.91 (s, 1H); $^{13}C$ NMR (176 MHz, $CDCl_3$) δ 18.3, 24.8, 28.1, 28.2, 28.4, 32.4, 32.7, 41.1, 45.2, 48.1, 48.4, 53.4, 80.6, 81.3, 96.0, 112.9, 115.3, 119.2, 126.1, 130.6, 132.0, 132.7, 135.4, 140.2, 150.6, 165.9, 168.7, 171.8.

Example 4: Synthesis of Building Block Compound, 96

Figure 5:
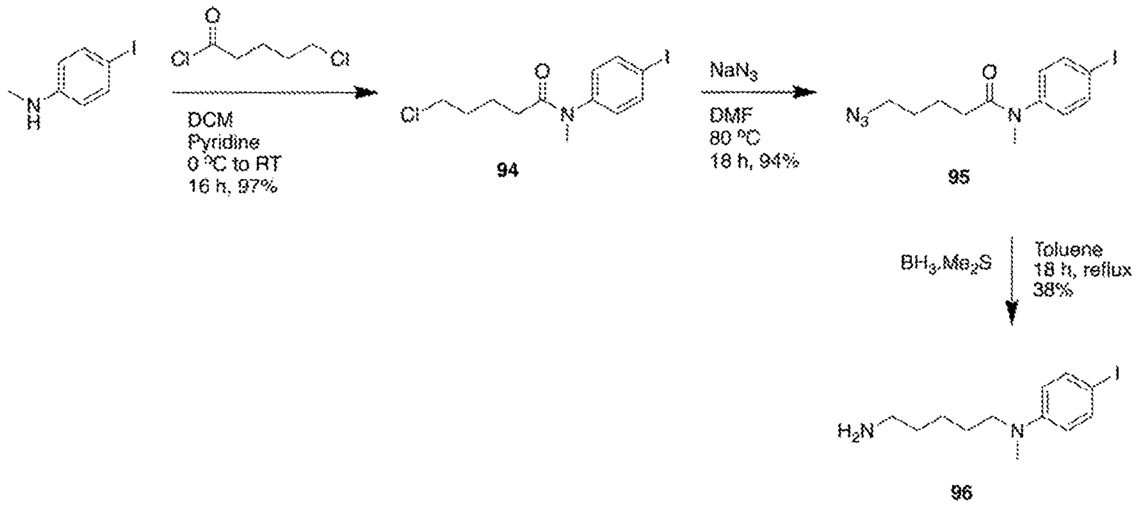
FIG. 5 shows the synthesis of a building block compound (96)

The synthesis of N-(5-Aminopentyl)-4-iodo-N-methylaniline, 96 is shown in FIG. 5 and detailed below.

Example 4.1

Synthesis of 5-Chloro-N-(4-iodophenyl)-N-methylpentanamide, 94

N-Methyl-4-iodoaniline (24.04 g, 103 mmol) was dissolved in dichloromethane (300 mL) and the solution was cooled to 0° C. 5-Chlorovaleryl chloride (14.6 mL, 113.3 mmol), then pyridine (9.16 mL, 113.3 mmol) were added and the resultant solution was stirred at RT for 16 h. The solution was diluted with dichloromethane and the organics were washed with sat. $NH_4Cl$ and $H_2O$, dried ($MgSO_4$) and evaporated to give a crude brown oil (40 g). This was purified by $SiO_2$ chromatography (7:3 cyclohexane/ethyl acetate) to give compound 94 as a yellow oil (35.16 g, 97%): 1H NMR (400 MHz, $CDCl_3$) δ 1.57-1.79 (m, 4H), 1.98-2.19 (m, 2H), 3.24 (s, 3H), 3.35-3.52 (m, 2H), 6.93 (d, J=7.9 Hz, 2H), 7.75 (d, J=8.0 Hz, 2H).

Example 4.2

Synthesis of 5-Azido-N-(4-iodophenyl)-N-methylpentanamide, 95

Compound 94 (35.0 g, 99.5 mmol) was dissolved in N,N-dimethylformamide (200 mL) and sodium azide (13.53 g, 208.95 mmol) was added, whereupon the solution was stirred at 80° C. for 18 h. The suspension was cooled, diluted with $H_2O$ and then extracted with EtOAc. The organics were washed with $H_2O$ and brine, dried ($MgSO_4$) and evaporated to give a crude orange oil (37.6 g). This was purified by $SiO_2$ chromatography (7:3 cyclohexane/ethyl acetate) to give compound 95 as an orange oil (33.4 g, 94%): 1H NMR (400 MHz, $CDCl_3$) δ 1.45-1.59 (m, 2H), 1.61-1.69 (m, 2H), 1.91-2.20 (m, 2H), 3.10-3.36 (m, 5H), 6.85-7.02 (m, 2H), 7.67-7.84 (m, 2H).

Example 4.3

Synthesis of N-(5-Aminopentyl)-4-iodo-N-methylaniline. 96

Compound 95 (5.24 g, 14.6 mmol) was dissolved in toluene (80 mL) and $BH_3 \cdot Me_2S$ (2.0 M in toluene, 16.8 mL, 33.6 mmol) was added, whereupon the solution was stirred at reflux for 16 h. The mixture was cooled, then stirred with 10% w/v aq. $Na_2CO_3$ for 0.5 h. The mixture was diluted with ethyl acetate and the organics were washed with $H_2O$ and brine, dried ($MgSO_4$) and evaporated to give a crude yellow oil (4.21 g). This was purified by $SiO_2$ chromatography (9:1 dichloromethane/methanol, 2% triethylamine) to give compound 96 as a clear oil that was carried immediately to the next step (1.76 g, 38%): 1H NMR (400 MHz, $CDCl_3$) δ 1.28-1.39 (m, 2H), 1.43-1.53 (m, 2H), 1.53-1.61 (m, 2H), 1.97 (s, 2H), 2.70 (t, J=7.0 Hz, 2H), 2.88 (s, 3H), 3.21-3.32 (m, 2H), 6.41-6.47 (m, 2H), 7.39-7.46 (m, 2H); $^{13}C$ NMR (101 MHz, $CDCl_3$) δ 24.3, 26.4, 33.1, 38.2, 41.9, 52.5, 76.4, 114.3, 137.6, 148.7.

Example 5: Synthesis of Building Block Compound, 99

Figure 6:
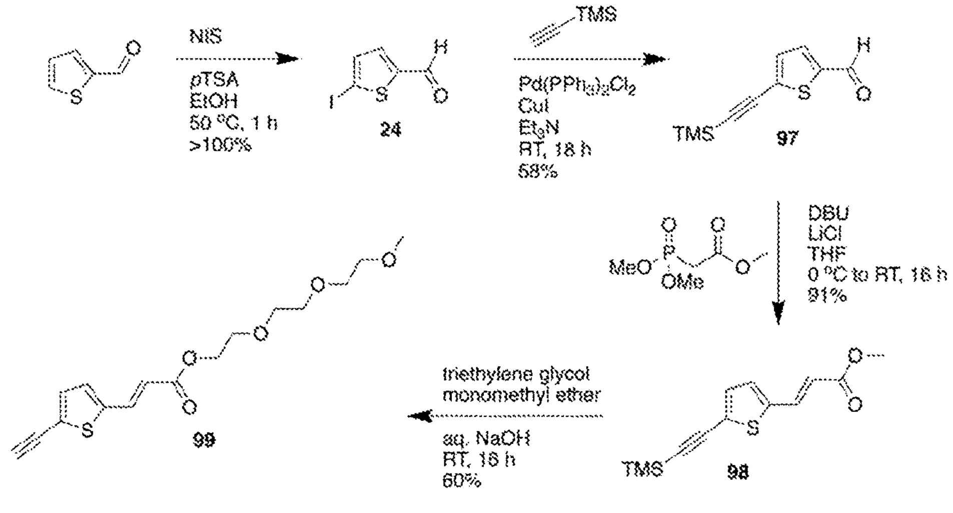
FIG. 6 shows the synthesis of a building block compound (99)

The synthesis of 2-[2-(2-Methoxyethoxy)ethoxy]ethyl (2E)-3-(5-ethynylthiophen-2-yl)prop-2-enoate, is shown in FIG. 6 and detailed below.

Example 5.1

Synthesis of 5-Iodothiophene-2-carbaldehyde, 24

To a solution of 2-thiophenecarboxaldehyde (9.34 mL, 100.0 mmol) in ethanol (50 mL) at 50° C. was added N-iodosuccinimide (24.75 g, 110.0 mmol) and para-toluenesulfonic acid monohydrate (1.90 g, 10.0 mmol), whereupon the resultant solution was stirred at 50° C. for 1 h. 1.0 M HCl (80 mL) was added, and the mixture was extracted with ethyl acetate, washed with sat. $Na_2S_2O_3$, $H_2O$ and brine, dried ($MgSO_4$) and evaporated to give compound 24 as a yellow oil that slowly crystallised (25.26 g, >100%): $^1H$ NMR (400 MHz, $CDCl_3$) δ 7.39 (s, 2H), 9.77 (s, 1H).

Example 5.2

Synthesis of 5-[2-(Trimethylsilyl)ethynyl]thiophene-2-carbaldehyde, 97

Triethylamine (300 mL) was degassed by sparging with argon for 1 h. Compound 24 (25 g, 105 mmol), trimethylsilylacetylene (16.0 mL, 115.5 mmol), $Pd(PPh_3)_2Cl_2$ (740 mg, 1.05 mmol) and CuI (200 mg, 1.05 mmol) were then added under argon and the resultant suspension was stirred at RT for 18 h. The mixture was diluted with diethyl ether and passed through Celite/$SiO_2$ to give a crude brown oil (17.7 g). This was purified by $SiO_2$ chromatography to give compound 97 as an orange oil that slowly crystallises (12.79 g, 58%): $^1H$ NMR (400 MHz, $CDCl_3$) δ 0.25 (s, 9H), 7.24 (d, J=4.0 Hz, 1H), 7.60 (d, J=4.0 Hz, 1H), 9.83 (s, 1H); $^{13}C$ NMR (101 MHz, $CDCl_3$) δ −0.5, 26.9, 96.3, 104.6, 132.5, 133.1, 135.7, 143.8, 182.4; IR (ATR) $v_{max}/cm^{-1}$ 2960w, 2899w, 2833w, 2148m, 1666s, 1438s, 1249s, 1223s, 1207s, 838s; MS (ES) m/z=209.0 $[M+H]^+$; HRMS (ES) calcd. for $C_{10}H_{13}SOSi$ $[M+H]^+$: 209.0451, found 209.0454.

Example 5.3

Synthesis of Methyl (2E)-3-{5-[2-(trimethylsilyl) ethynyl]thiophen-2-yl}prop-2-enoate, 98

Trimethylphosphonoacetate (14.0 mL, 86.4 mmol) and LiCl (3.66 g, 86.4 mmol) were added to anhydrous tetrahydrofuran (250 mL) at 0° C. and the resultant solution was stirred for 15 min, whereupon compound 97 (15.0 g, 72 mmol) was added. To this solution was slowly added 1,8-diazabicyclo[5.4.0]undec-7-ene (12.9 mL, 86.4 mmol), and the resultant slurry was stirred at RT for 16 h. This was poured into crushed ice and extracted with ethyl acetate. The organics were washed with $H_2O$ and brine, dried ($MgSO_4$) and evaporated to give a crude brown oil (21 g). This was purified by $SiO_2$ chromatography (9:1 cyclohexane/ethyl acetate) to give compound 98 as a light yellow solid (17.23 g, 91%): 1H NMR (400 MHz, $CDCl_3$) δ 0.24 (s, 9H), 3.78 (s, 3H), 6.19 (d, J=15.7 Hz, 1H), 7.05-7.14 (m, 2H), 7.67 (d, J=15.7 Hz, 1H); $^{13}C$ NMR (75 MHz, $CDCl_3$) δ −0.3, 51.7, 97.0, 101.9, 117.3, 125.8, 130.6, 133.3, 136.5, 140.4, 166.9; IR (ATR) $v_{max}/cm^{-1}$ 2953w, 2899w, 2144m, 1715s, 1621s, 1516w, 1432m, 1391w, 1301s, 1269s, 1202s, 1161s, 838s; MS(ES): m/z=265.1 $[M+H]^+$; HRMS (ES) calcd for $C_{13}H_{17}O_2SSi$ $[M+H]^+$: 265.0713, found 265.0713.

Example 5.4

Synthesis of 2-[2-(2-Methoxyethoxy)ethoxy]ethyl (2E)-3-(5-ethynylthiophen-2-yl)prop-2-enoate, 99

Compound 98 (13.03 g, 49.3 mmol) was dissolved in triethylene glycol monomethyl ether (50 mL), whereupon 20% aq. w/v NaOH (1.3 mL) was added. The resultant mixture was stirred at RT for 16 h whereupon the solution was diluted with ethyl acetate. The organics were washed with $H_2O$ and brine, dried ($MgSO_4$) and evaporated to give a crude dark oil (16 g). This was purified by $SiO_2$ chromatography (1:1 cyclohexane/ethyl acetate) to give compound 99 as a yellow oil that quickly darkens (8.18 g, 51%): 1H NMR (400 MHz, $CDCl_3$) δ 3.36 (s, 3H), 3.46 (s, 1H), 3.50-3.56 (m, 2H), 3.61-3.69 (m, 6H), 3.72-3.79 (m, 2H), 4.26-4.38 (m, 2H), 6.24 (d, J=15.7 Hz, 1H), 7.09 (d, J=3.8 Hz, 1H), 7.17 (d, J=3.8 Hz, 1H), 7.68 (dd, J=15.7, 0.6 Hz, 1H); $^{13}C$ NMR (101 MHz, $CDCl_3$) δ 59.0, 63.8, 69.1, 70.5, 70.6, 71.9, 83.7, 117.7, 124.6, 130.5, 133.8, 136.5, 140.8, 166.3; IR (ATR) $v_{max}/cm^{-1}$ 3241br, 3089w, 2874br, 2098w, 1705s, 1622s, 1516m, 1445m, 1342m, 1301m, 1264s, 1165s, 1100s, 807s; MS(ES): m/z=325.1 $[M+H]^+$; HRMS (ES) calcd for $C_{16}H_{21}O_5S$ $[M+H]^+$: 325.1104, found 325.1100.

Example 6: Synthesis of Light-Activated Compound, 100

Figure 7:
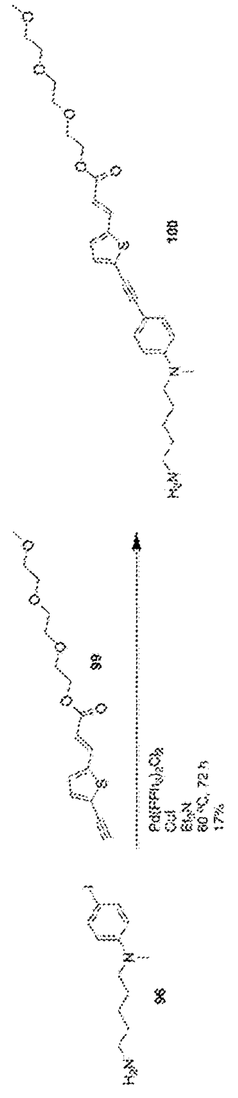
FIG. 7 shows the synthesis of light-activated compound (100)

The synthesis of light-activated compound 100 is shown in FIG. 7 and detailed below.

Synthesis of 2-[2-(2-Methoxyethoxy)ethoxy]ethyl (2E)-3-[5-(2-{4-[(5-aminopentyl)(methyl) aminol phenyl}ethynyl)thiophen-2-yl]prop-2-enoate, 100

Compound 96 (1.70 g, 5.34 mmol) and compound 99 (2.42 g, 7.48 mmol) were dissolved in triethylamine (80 mL) and the solution was degassed by sparging with argon for 1 h. $Pd(PPh_3)_2Cl_2$ (372 mg, 0.53 mmol) and CuI (100 mg, 0.53 mmol) were then added under argon and the resultant suspension was stirred at 60° C. for 72 h. The resultant suspension was diluted with dichloromethane and washed with sat. $NaHCO_3$ and water, dried ($MgSO_4$) and evaporated to give a crude dark oil (3.75 g). This was purified by $SiO_2$ chromatography (95:5 dichloromethane/methanol, 1% triethylamine) to give compound 100 as a light orange solid (0.47 g, 17%): $^1H$ NMR (400 MHz, $CDCl_3$) δ 1.32-1.41 (m, 2H), 1.54-1.64 (m, 4H), 2.81 (t, J=7.2 Hz, 2H), 2.95 (s, 3H), 3.30-3.35 (m, 2H), 3.37 (s, 3H), 3.53-3.56 (m, 2H), 3.64-3.69 (m, 6H), 3.75-3.79 (m, 2H), 4.29-4.39 (m, 2H), 6.20 (d, J=15.7 Hz, 1H), 6.56-6.65 (m, 2H), 7.07-7.14 (m, 2H), 7.31-7.40 (m, 2H), 7.70 (dd, J=15.7, 0.6 Hz, 1H); $^{13}C$ NMR (101 MHz, $CDCl_3$) δ 24.2, 26.5, 31.0, 38.3, 41.1, 52.2, 59.0, 63.7, 69.2, 70.6, 70.6, 71.9, 80.6, 97.7, 108.3, 111.4, 116.4, 127.6, 131.3, 131.5, 132.8, 137.0, 139.4, 149.2, 166.7; IR (ATR) $v_{max}/cm^{-1}$ 2925m, 2871m, 2189w, 1738m, 1712m, 1604s, 1530s, 1511m, 1376m, 1196m; MS(ASAP): m/z=515.2 $[M+H]^+$; HRMS (ASAP) calcd for $C_{28}H_{39}N_2O_5S$ $[M+H]^+$: 515.2574, found 515.2569.

Example 7: Synthesis of Protected HDAC Inhibitor Compound, 101

Figure 8:
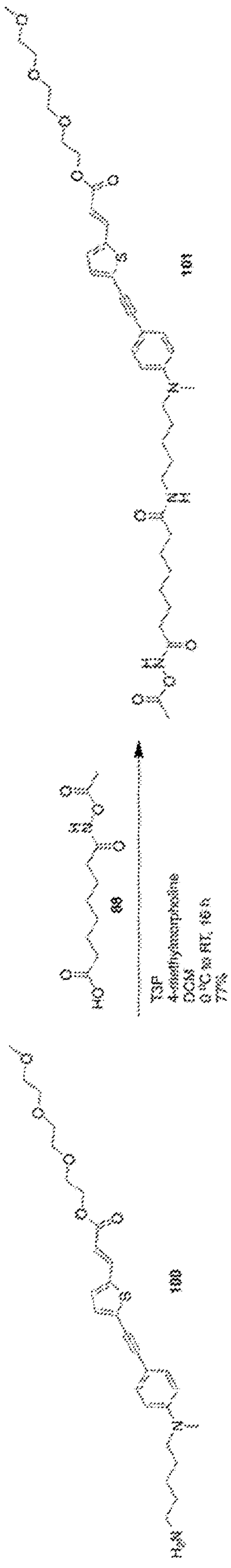
FIG. 8 shows the synthesis of exemplary compound (101)

The synthesis of protected HDAC inhibitor compound 101 with light-activated cell killing activity is shown in FIG. 8 and detailed below:

Synthesis of 2-[2-(2-Methoxyethoxy)ethoxy]ethyl (2E)-3-[5-(2-{4-[(5-{7-[(acetyloxy) carbamoyl] heptanamido}pentyl)(methyl)amino]phenyl}ethynyl) thiophen-2-yl]prop-2-enoate, 101

Compound 100 (128 mg, 0.25 mmol) was dissolved in dichloromethane (10 mL) and the solution was cooled to 0° C., whereupon 4-methylmorpholine (0.055 mL, 0.5 mmol), compound 88 (76 mg, 0.33 mmol) and propylphosphonic anhydride (50% wt. in ethyl acetate, 0.32 mL, 0.5 mmol) were added and the resultant mixture was stirred at RT for 16 h. The mixture was diluted with dichloromethane, washed with $H_2O$, dried ($MgSO_4$) and evaporated to give a crude yellow oil. This was purified by $SiO_2$ chromatography (95:5, dichloromethane/methanol) to give compound 101 as a yellow oil (141 mg, 77%): $^1H$ NMR (400 MHz, $CDCl_3$) δ 1.30-1.42 (m, 6H), 1.46-1.55 (m, 2H), 1.55-1.63 (m, 4H), 1.64-1.72 (m, 2H), 2.11-2.17 (m, 2H), 2.20 (s, 3H), 2.23 (t, J=7.3 Hz, 2H), 2.95 (s, 3H), 3.17-3.26 (m, 2H), 3.33 (t, J=7.3 Hz, 2H), 3.37 (s, 3H), 3.51-3.57 (m, 2H), 3.63-3.70 (m, 6H), 3.71-3.80 (m, 2H), 4.26-4.40 (m, 2H), 5.64 (s, 1H), 6.20 (d, J=15.6 Hz, 1H), 6.61 (d, J=5.4 Hz, 2H), 7.09 (d, J=3.8 Hz, 1H), 7.11 (d, J=3.9 Hz, 1H), 7.31-7.41 (m, 2H), 7.70 (dd, J=15.7, 0.6 Hz, 1H), 9.55 (s, 1H); $^{13}C$ NMR (101 MHz, $CDCl_3$) δ 18.3, 24.3, 24.7, 25.3, 26.5, 26.9, 28.0, 28.2, 29.5, 32.5, 36.2, 38.3, 39.3, 52.2, 53.4, 59.0, 63.7, 69.2, 70.5, 70.6, 70.6, 71.9, 77.0, 80.7, 97.6, 111.4, 116.4, 127.5, 131.3, 131.5, 132.8, 137.0, 139.4, 148.2, 166.7, 168.8, 173.3; IR (ATR) $v_{max}/cm^{-1}$ 3304br, 2927m, 2860m, 2189m, 1708m, 1645m, 1619s, 1603s, 1529s, 1512m, 1367m, 1242m, 1193s, 1137s, 1110m, 852m; MS(ES): m/z=728.3 $[M+H]^+$; HRMS (ES) calcd for $C_{38}H_{54}N_3O_9S$ $[M+H]^+$: 728.3575, found 728.3578.

Example 8: Fluorescein Diacetate Cellular Viability Assay

A fluorescein diacetate cellular viability assay measuring the viability of HaCaT keratinocytes in response to treatment with compound 92 without irradiation (no light) and when irradiated (Light) was carried out as follows:

HaCaT keratinocyte cells were seeded in two 96 well plates and incubated for 24 h at 37° C. 5% $CO_2$. The incubating media was removed and compound 92 was added at a range of concentrations, along with a dimethyl sulfoxide (DMSO) control, before the cells were incubated for one hour at 37° C. 5% $CO_2$, whereupon one plate was irradiated at 405 nm for 5 min (72 $mW/cm^2$). Both plates were then incubated at 37° C. 5% $CO_2$ for 24 h. The media was removed, and cells were washed with 1× phosphate buffered saline (PBS), then fluorescein diacetate (FDA) was added, and the cells were incubated at RT, in the dark, for 10 min.

Figure 9:
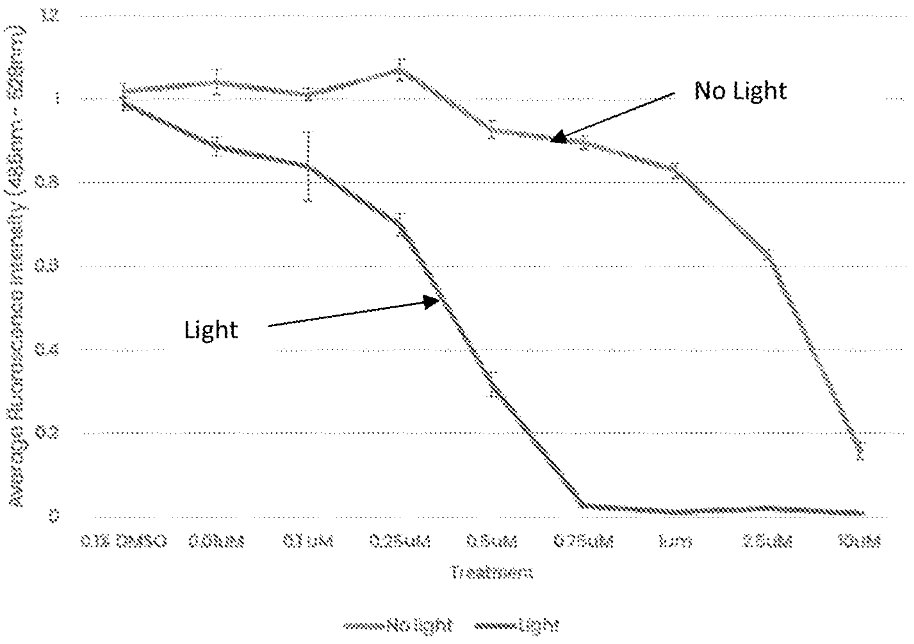
FIG. 9 shows the results of a fluorescein diacetate cellular viability assay measuring the viability of HaCaT keratinocytes in response to treatment with compound 92 with and without irradiation.

The fluorescein diacetate stain was then removed, and cells were washed with 1× phosphate buffered saline. The plates were read at 485/520 nm to determine cell viability at differing treatment concentrations of compound 92 with and without light exposure. The results are shown in FIG. 9, and demonstrate that light activation causes cell death at low concentrations ($IC_{50}$=0.69 pM). Cell viability is reduced at higher concentrations ($IC_{50}$=5.50 μM) without light activation due to HDAC inhibition activity in response to enzymatic metabolism.

Example 9: Immunofluorescence Imaging

Immunofluorescence imaging of HaCaT keratinocytes treated with compound 92 (5 μM) and ethanol (EtOH), and co-treated with an anti-acetyl-H3 primary antibody that detects the presence of acetylated H3 histones was carried out as follows:

50,000 HaCaT cells were plated on coverslips and grown for 2 days before compound 92 (5 pM) was added and incubated at RT for 30 min. Cells were washed in phosphate buffered saline then fixed in 4% PFA. Cells were washed again with phosphate buffered saline before blocking and permeabilization with 0.3% triton 100-X/5% goat serum in phosphate buffered saline for 60 min. Cells were then washed with phosphate buffered saline and anti-acetyl-histone 3 antibody was added and incubated overnight at 4° C. Second antibody (Alexa-594 anti-rabbit) was added for 45 min before cells were washed again and mounted for imaging.

Figure 10:
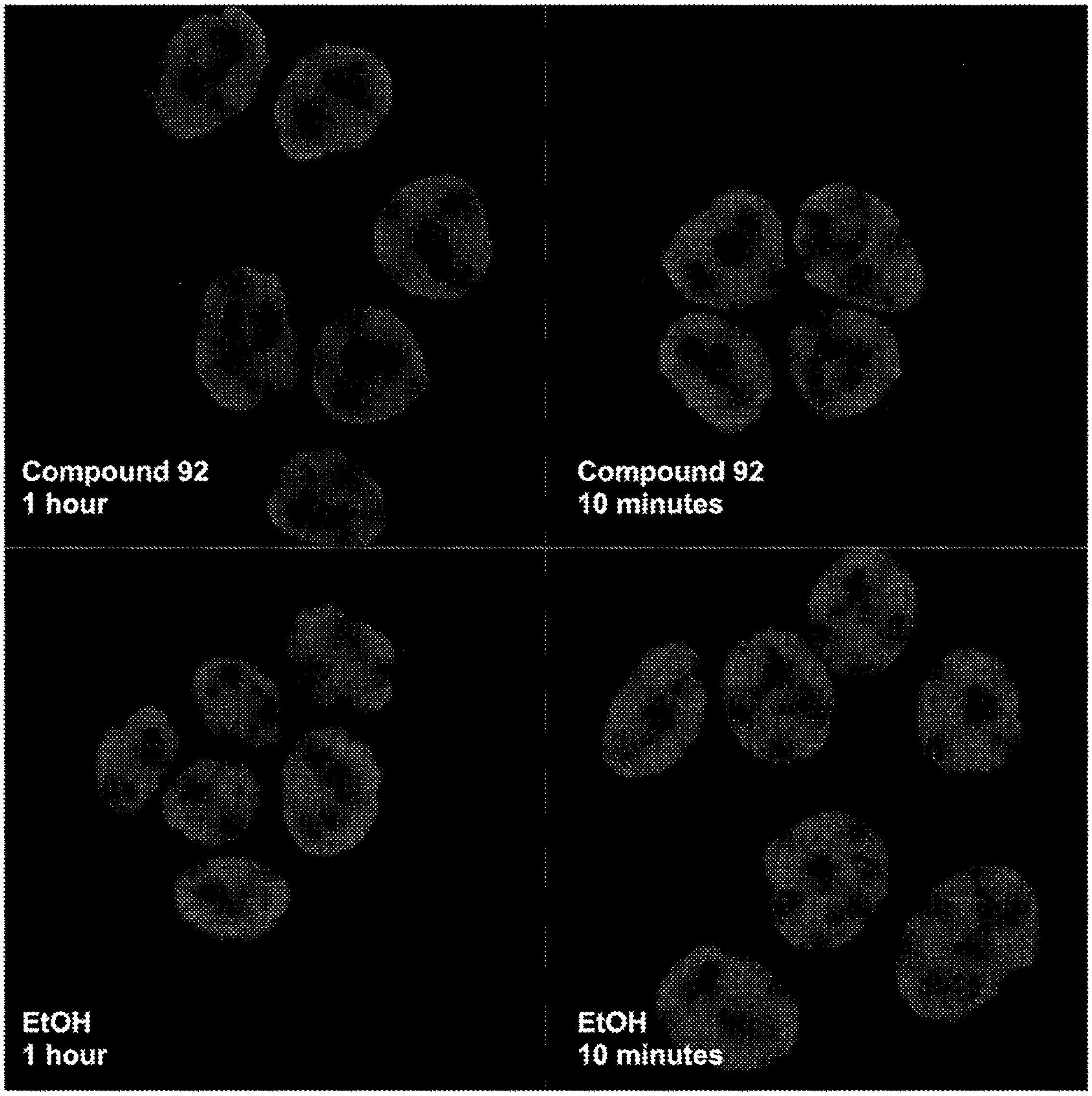
FIG. 10 shows immunofluorescence imaging of HaCaT keratinocytes treated with compound 92 and EtOH, and co-treated with an anti-acetyl-H3 primary antibody that detected the presence of acetylated H3 histones.

The results are shown in FIG. 10. From this it can be seen that compound 92 displays limited activity after ten minutes but, after one hour, cells exhibit the characteristic nuclear ring phenotype that is indicative of the build-up of acetylated H3 in response to inhibition of HDAC enzymes. This delayed behaviour is indicative of an initial lag phase as compound 92 is enzymatically metabolised to the active form. Ethanol-treated cells do not exhibit this nuclear ring phenotype at either time point.

Example 10: Acetyl-H3 Abundance in Treated SCC-4 Cells

Figure 11:
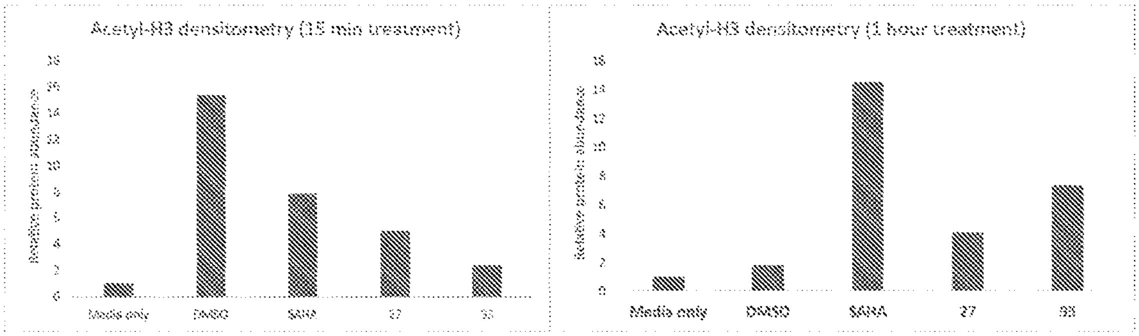
FIG. 11 shows the abundance of acetyl-H3 in SCC-4 cells in response to treatment after 15 minutes and after one hour with compound 93 according to the invention, and with control compounds.

To measure acetyl-H3 protein abundance in SCC-4 cells, cells were seeded at 350,000 cells/well of a 6-well plate. The following day, cells were treated with compounds or controls. After 15 minutes and/or 1 hour of treatment, the cells were lysed in RIPA buffer. SDS-PAGE was performed using Any kD™ Mini-PROTEAN® TGX™ Precast Protein Gels on the cell lysate to separate the proteins. Proteins were subsequently transferred onto a PVDF membrane (Macherey-Nagel) before blocking in TBST containing 5% milk and 2.5% fish skin gelatin. Primary (acetyl-H3, 9677S, CST and α-tubulin, T5168, Sigma) and secondary antibodies (goat anti-rabbit IgG, A6154, Sigma and goat anti-mouse, SA00001-1, Proteintech) were diluted in blocking buffer and stained for 1 hour each at room temperature with TBST washes between steps. A chemiluminescence signal was measured using an iBright imager (Invitrogen). Acetyl-H3 levels were normalised and the resulting densitometry measurements (measured using ImageJ software) are shown in FIGS. 11 to 13. Image analysis was performed using ImageJ software.

FIG. 11 shows densitometry measurements of acetyl-H3 after 15 minutes and 1 hour of treatment with media, DMSO (dimethyl sulfoxide), SAHA (suberoylanilide hydroxamic acid), compound 27 and compound 93. The acetyl-H3 levels were normalised against α-tubulin (15 minutes) and AC-40 (1 hour).

FIG. 12 shows densitometry measurements of acetyl-H3 after 1 hour of treatment with media, DMSO (dimethyl sulfoxide), SAHA (suberoylanilide hydroxamic acid), compound 27, compound 93 and compound 101. The acetyl-H3 levels were normalised against α-tubulin.

FIG. 13 shows densitometry measurements of acetyl-H3 after 15 minutes of treatment with media, DMSO (dimethyl sulfoxide), SAHA (suberoylanilide hydroxamic acid), compound 27 and compound 92. The acetyl-H3 levels were normalised against α-tubulin.

Example 11: Expression of Caspase-3 in Treated HaCaT Cells

HaCaT cells were seeded at 50,000 cells per well on coverslips in 6-well plates. The following day, cells were treated with 50 nM and 100 nM of compound 93 for 30 minutes. DMSO was used as a control. Light activation was carried out by irradiation using a PhotoReact 365 which was modified to emit light at 405 nm at 29 mW/cm$^2$ over 5 minutes. The following day, cells were then fixed using 4% PFA, permeabilised using Triton X-100/Tween 20, blocked in blocking buffer (5% BSA and 0.1% Tween 20 in PBS). Primary (caspase-3, ab13847, Abcam) and secondary antibodies (goat anti-rabbit IgG Alexa Fluor 594) were diluted in PBS containing 5% goat serum and 0.1% Tween 20. Coverslips were added to the slides and imaged on a Zeiss LSCM 880. Image analysis was performed using ImageJ software. FIG. 14 shows caspase-3 expression in HaCaT cells treated with DMSO, 50 nM compound 93, and 100 nM compound 93 and quantification of expression levels.

Example 12: Co-Localisation of Compounds in SCC-4 Cells

SCC-4 cells were seeded at 50,000 cells/well on 8-well chamber slides. The following day, cells were treated with 1 μM compound 101 and 1 μM compound 93 for 1 hour. Cells were changed to live cell imaging solution media. Co-stains (MitoTracker, Bodipy ER Tracker, LipidSpot 610 or LysoTracker) were added to cells 30 minutes before imaging. Imaging was carried out using a Zeiss LSCM 880 and image analysis was performed on ImageJ.

FIG. 15 shows co-localisation of compound 101 with mitochondria (MitoTracker), lipid droplets (LipidSpot610) and acidic organelles (LysoTracker) of SCC-4 cells. Pearson's Coefficient was calculated to demonstrate the correlation between the compound localisation and co-stain localisation and the results are shown in Table 1.

TABLE 1

Correlation between compound localisation and co-stain localisation.

| Co-stain | N | Pearson's R Value (no threshold) | Pearson's R Value (above threshold) |
|---|---|---|---|
| MitoTracker | 3 | 0.55 +/− 0.04 | 0.30 +/− 0.11 |
| LipidSpot 610 | 1 | 0.30 | 0.08 |
| LysoTracker | 1 | 0.64 | 0.54 |

FIG. 16 shows co-localisation of compound 93 with mitochondria (MitoTracker), endoplasmic reticulum (Bodipy ER Tracker), lipid droplets (LipidSpot610) and acidic organelles (LysoTracker) of SCC-4 cells. Pearson's Coefficient was calculated to demonstrate the correlation between the compound localisation and co-stain localisation and the results are shown in Table 2.

TABLE 2

Correlation between compound localisation and co-stain localisation.

| Co-stain | N | Pearson's R Value (no threshold) | Pearson's R Value (above threshold) |
|---|---|---|---|
| MitoTracker | 3 | 0.27 +/− 0.03 | −0.13 +/− 0.07 |
| LipidSpot 610 | 3 | 0.10 +/− 0.02 | −0.13 +/− 0.02 |
| Bodipy ER-Tracker Red | 3 | 0.36 +/− 0.09 | 0.0 +/− 0.1 |
| LysoTracker | 2 | 0.27 +/− 0.02 | 0.13 +/− 0.05 |

Example 13: Deprotection of Compound 93

The deprotection of compound 93 to yield Tert-butyl (2E)-3-{5-[2-(4-{4-[7-(hydroxycarbamoyl)heptanoyl]piperazin-1-yl}phenyl)ethynyl]thiophen-2-yl}prop-2-enoate, 103 is shown in FIG. 17 and described below.

Compound 93 (500 mg, 0.82 mmol) was dissolved in methanol (30 mL) whereupon NaOH (32 mg, 0.82 mmol, as solution in $H_2O$, 1 mL) was added and the resultant solution was stirred for 5 h at room temperature. The mixture was diluted with dichloromethane and the organics were washed with $H_2O$, dried ($MgSO_4$) and evaporated to give a crude yellow solid. This was purified by recrystallisation from acetonitrile to give compound 103 as a yellow solid (170 mg, 36%): $^1$H NMR (700 MHz, dimethyl sulfoxide-$d_6$) δ 1.22-1.29 (m, 4H), 1.47 (s, 9H), 1.47-1.52 (m, 4H), 1.94 (t, J=7.4 Hz, 2H), 2.32 (t, J=7.5 Hz, 2H), 3.20-3.25 (m, 2H), 3.25-3.29 (m, 2H), 3.55-3.60 (m, 4H), 6.18 (d, J=15.7 Hz, 1H), 6.91-7.00 (m, 2H), 7.31 (d, J=3.8 Hz, 1H), 7.37-7.44 (m, 2H), 7.48 (d, J=3.8 Hz, 1H), 7.66 (d, J=15.8 Hz, 1H), 8.64 (s, 1H), 10.32 (s, 1H); $^{13}$C NMR (176 MHz, dimethyl sulfoxide-$d_6$) δ 24.6, 25.0, 27.8, 28.4, 28.5, 32.1, 32.2, 40.5, 44.4, 46.8, 47.2, 80.1, 80.9, 96.6, 110.2, 114.7, 118.9, 125.3, 132.1, 132.4, 132.7, 135.5, 139.6, 150.7, 165.0, 169.1, 170.7; IR (ATR) $v_{max}$/cm-13207br, 2977w, 2930w, 2858w, 2194w, 1698m, 1619s, 1603s, 1526m, 1508m, 1231s, 1145s, 754m; MS (ASAP) m/z=566.2 [M+H]$^+$; HRMS (ASAP) calcd. for $C_{31}H_{40}N_3O_5S$ [M+H]$^+$: 566.2683, found 566.2683.

All of the features disclosed in this specification (including any accompanying claims, abstract and drawings), and/or all of the steps of any method or process so disclosed, may be combined in any combination, except combinations where at least some of such features and/or steps are mutually exclusive. Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A compound of formula I:

Formula 1

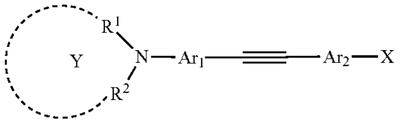

in which:

$R^1$ is H or an alkyl group comprising 1 to 10 carbon atoms; $R^2$ is P—Z, in which P is an alkyl group comprising from 1 to 15 carbon atoms, optionally substituted with one or more of N atoms, —C═O, and —NHC═O; and Z is:

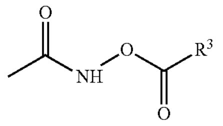

in which $R^3$ is H, a $C_1$-$C_9$ alkyl, $—CH_2OH$, $—CH_2OCH_3$, -Ph, $—C_6H_4OH$, $—CH(CH_3)OH$, $—C(CH_2COOH)_2OH$, $—C(═O)CH_3$, $—CH_2NH_2$, $—CH_2NH(C═O)CH_2NH_2$, or $—CH_2NH(C═O)CH_2NH(C═O)CH_2NH_2$;

Or $R^1$ and $R^2$ form part of a heterocyclic group Y having 5 or 6 members and being substituted with P-Z, wherein P is as defined above, and wherein Z is as defined above;

$Ar_1$ and $Ar_2$ are each, independently, selected from a phenyl, pyridine, pyrimidine, thiophene, furan, benzofuran or thiazole group; and X is —C═C—C(═O)$OR^4$, in which $R^4$ is an alkyl group comprising from 1 to 10 carbon atoms, optionally substituted with one or more O atoms.

2. A compound of formula I as claimed in claim 1, in which $R_3$ is a $C_1$-$C_3$ alkyl.

3. A compound of formula I as claimed in claim 2, in which $R_3$ is $—CH_3$.

4. A compound of formula I as claimed in claim 1, in which $Ar^1$ is thiazole or phenyl.

5. A compound of formula I as claimed in claim 1, in which $Ar^2$ is pyridine, thiophene, or furan.

6. A compound of formula I as claimed in claim 1, in which $R^1$ and $R^2$ form part of a heterocyclic group Y, optionally wherein Y is piperazine.

7. A compound of formula I as claimed in claim 6, in which P is a $C_1$-$C_{15}$ alkyl group substituted with —C(═O).

8. A compound of formula I as claimed in claim 7, in which P is $—C(═O)(CH_2)_6$.

9. A compound of formula I as claimed in claim 1, in which $R^4$ is an alkyl group.

10. A compound of formula I as claimed in claim 9, in which $R^4$ is $—CH_3$, $—C(CH_3)_3$ or $—CH_2CH(CH_3)_2$.

11. A compound of formula I as claimed in claim 1, in which $R^1$ is $C_1$-$C_3$ alkyl, optionally wherein $R^1$ is $—CH_3$.

12. A compound of formula I as claimed in claim 1, or as claimed in claim 11, in which $R^2$ is P—Z, in which P is a $C_1$-Cis alkyl substituted with —NHC(═O).

13. A compound of formula I as claimed in claim 12, in which P is $—(CH_2)_5NHC(═O)(CH_2)_6$.

14. A compound of formula I as claimed in claim 1, in which $R^4$ is $—(CH_2CH_2O)_nCH_3$ in which n is an integer between 1 and 8, optionally wherein $R^4$ is $—(CH_2CH_2O)_3CH_3$.

15. A compound of formula I as claimed in claim 1, wherein the compound is selected from compound 92, compound 93, compound 101 and compound 102:

92

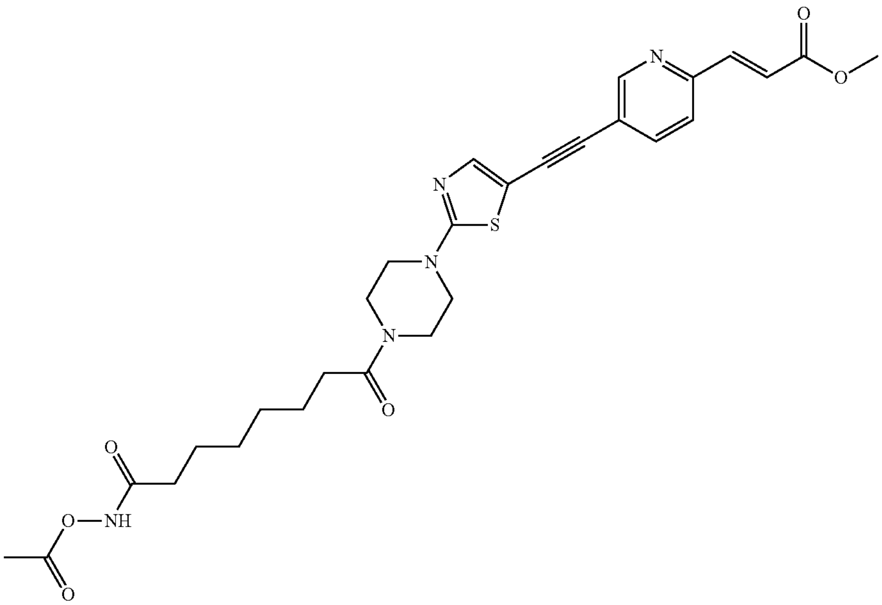

-continued
93
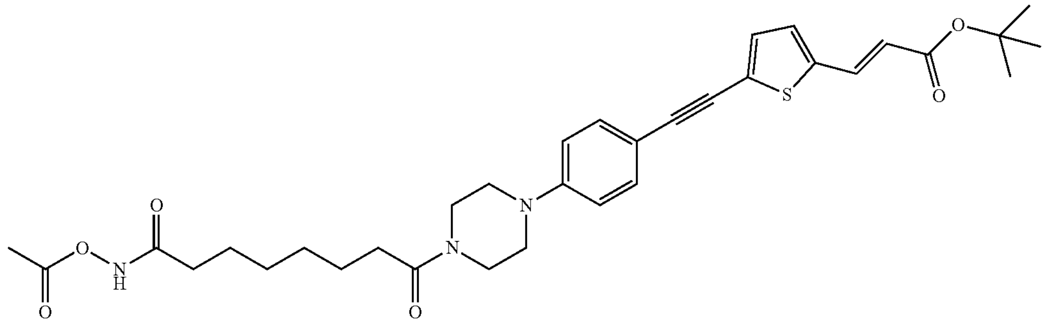
101
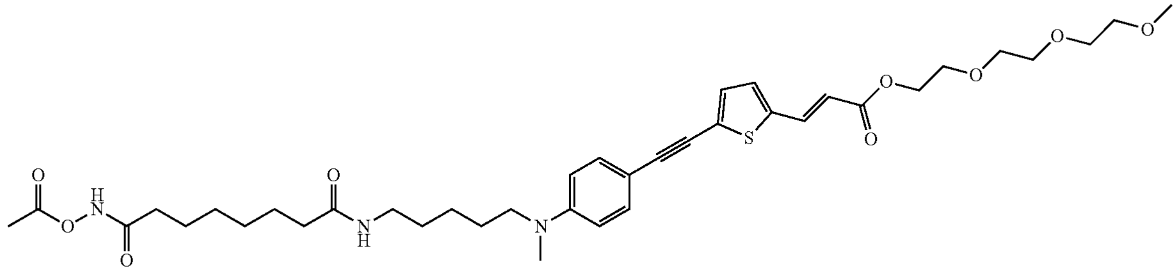
102
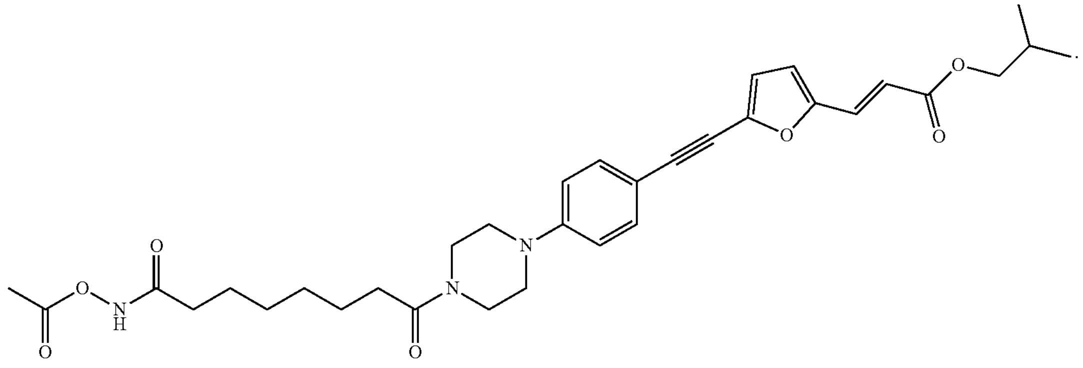
16. A pharmaceutical composition comprising a compound of formula I as claimed in claim 1, optionally in combination with one or more pharmaceutically acceptable excipients, diluents or carriers.
* * * * *